United States Patent
Slatkine et al.

(10) Patent No.: US 7,740,600 B2
(45) Date of Patent: Jun. 22, 2010

(54) APPARATUS AND METHOD FOR INHIBITING PAIN SIGNALS TRANSMITTED DURING A SKIN RELATED MEDICAL TREATMENT

(75) Inventors: Michael Slatkine, Herzlia (IL); Raphael Shavit, Tel Aviv (IL)

(73) Assignee: Candela Corporation, Wayland, MA (US)

( * ) Notice: Subject to any disclaimer, the term of this patent is extended or adjusted under 35 U.S.C. 154(b) by 993 days.

(21) Appl. No.: 11/498,456

(22) Filed: Aug. 3, 2006

(65) Prior Publication Data

US 2006/0293722 A1 Dec. 28, 2006

Related U.S. Application Data

(63) Continuation-in-part of application No. 11/401,674, filed on Apr. 11, 2006, which is a continuation-in-part of application No. 11/057,542, filed on Feb. 14, 2005, and a continuation-in-part of application No. 10/498,382, filed on Jun. 10, 2004, which is a continuation-in-part of application No. PCT/IL02/00635, filed on Aug. 2, 2002.

(30) Foreign Application Priority Data

| Feb. 22, 2004 | (IL) | 160510 |
| Apr. 12, 2005 | (EP) | 05007952 |
| Aug. 4, 2005 | (IL) | 170132 |
| Apr. 6, 2006 | (IL) | 174847 |
| May 8, 2006 | (IL) | 175486 |

(51) Int. Cl.
*A61H 7/00* (2006.01)

(52) U.S. Cl. .......................................... 601/6; 601/7

(58) Field of Classification Search ................ 606/9–10; 601/7, 10, 15, DIG. 1, DIG. 4, DIG. 5, 6
See application file for complete search history.

(56) References Cited

U.S. PATENT DOCUMENTS 3,982,541 A 9/1976 L'Esperance, Jr.

(Continued)

FOREIGN PATENT DOCUMENTS

DE 37 30 469 A1 6/1988

(Continued)

OTHER PUBLICATIONS

Effects of Tissue Optical Clearning,...,Lasers Light within Tissue (G. Vergas & A.J. Welch, "Laser in Surgery and Medicine", Supp. 13, 2001, p. 26).

(Continued)

*Primary Examiner*—Michael A. Brown
(74) *Attorney, Agent, or Firm*—Proskauer Rose LLP

(57) ABSTRACT

An apparatus adapted to inhibit pain signals generated by pain receptors in the skin during a skin related medical treatment such as an injection. An evacuation chamber is provided with an essentially rigid interface element larger than a threshold surface area through which a medical treatment can be administered to a selected skin region, one or more walls which are placeable in the vicinity of the skin region, an interior defined by the walls and by the interface element, and an opening at the bottom of the interior which is sealable by the skin region. A device generates a vacuum within the evacuation chamber interior to a level greater than the threshold vacuum level suitable for drawing the skin region through the opening towards, and in a compressing relation against, the interface element, to inhibit the transmission of a pain signal generated by pain receptors located within the skin region.

53 Claims, 23 Drawing Sheets

U.S. PATENT DOCUMENTS

| | | | |
|---|---|---|---|
| 4,518,387 A * | 5/1985 | Murphy et al. | 604/187 |
| 4,592,353 A | 6/1986 | Daikuzono | |
| 4,736,743 A | 4/1988 | Daikuzono | |
| 4,976,709 A | 12/1990 | Sand | |
| 5,057,104 A | 10/1991 | Chess | |
| 5,059,192 A | 10/1991 | Zaias | |
| 5,066,293 A | 11/1991 | Furumoto | |
| 5,217,455 A | 6/1993 | Tan | |
| 5,226,907 A | 7/1993 | Tankovich | |
| 5,282,797 A | 2/1994 | Chess | |
| 5,312,395 A | 5/1994 | Tan et al. | |
| 5,344,418 A | 9/1994 | Ghaffari | |
| 5,401,270 A | 3/1995 | Schoenborn | |
| 5,411,502 A | 5/1995 | Zair | |
| 5,431,647 A | 7/1995 | Purcell, Jr. et al. | |
| 5,449,354 A | 9/1995 | Konwitz et al. | |
| 5,527,308 A | 6/1996 | Anderson et al. | |
| 5,530,780 A | 6/1996 | Ohsawa | |
| 5,558,660 A | 9/1996 | Dreier | |
| 5,595,568 A | 1/1997 | Anderson et al. | |
| 5,626,631 A | 5/1997 | Eckhouse | |
| 5,630,811 A | 5/1997 | Miller | |
| 5,655,547 A | 8/1997 | Karni | |
| 5,735,844 A | 4/1998 | Anderson et al. | |
| 5,745,519 A | 4/1998 | Ruda et al. | |
| 5,814,041 A | 9/1998 | Anderson et al. | |
| 5,853,407 A | 12/1998 | Miller | |
| 5,871,521 A | 2/1999 | Kaneda et al. | |
| 5,879,346 A | 3/1999 | Waldman et al. | |
| 5,885,273 A | 3/1999 | Eckhouse et al. | |
| 5,947,957 A | 9/1999 | Morris | |
| 5,961,475 A | 10/1999 | Guitay | |
| 5,964,749 A | 10/1999 | Eckhouse | |
| 6,011,890 A | 1/2000 | Neuberger | |
| 6,096,029 A | 8/2000 | O'Donnell, Jr. | |
| 6,120,497 A | 9/2000 | Anderson et al. | |
| 6,132,392 A | 10/2000 | Stone | |
| 6,142,650 A | 11/2000 | Brown et al. | |
| 6,165,170 A | 12/2000 | Wynne et al. | |
| 6,197,020 B1 | 3/2001 | O'Donnell, Jr. | |
| 6,214,034 B1 | 4/2001 | Azar | |
| 6,261,310 B1 | 7/2001 | Neuberger et al. | |
| 6,264,649 B1 | 7/2001 | Whitcroft et al. | |
| 6,273,884 B1 | 8/2001 | Altshuler et al. | |
| 6,280,438 B1 | 8/2001 | Eckhouse et al. | |
| 6,530,920 B1 * | 3/2003 | Whitcroft et al. | 606/13 |
| 6,544,259 B1 | 4/2003 | Tsaliovich | |
| 6,662,054 B2 | 12/2003 | Kreindel et al. | |
| 2002/0013602 A1 | 1/2002 | Huttner | |
| 2002/0034012 A1 | 3/2002 | Santoro et al. | |
| 2002/0128600 A1 | 9/2002 | Nissels | |
| 2002/0128635 A1 | 9/2002 | Altshuler et al. | |
| 2002/0169442 A1 * | 11/2002 | Neev | 606/9 |
| 2003/0083536 A1 | 5/2003 | Eshel et al. | |
| 2004/0077977 A1 | 4/2004 | Ella et al. | |
| 2004/0082940 A1 | 4/2004 | Black et al. | |
| 2004/0254599 A1 | 12/2004 | Lipoma et al. | |
| 2005/0261584 A1 | 11/2005 | Eshel et al. | |
| 2007/0027411 A1 * | 2/2007 | Ella et al. | 601/7 |

FOREIGN PATENT DOCUMENTS

| | | |
|---|---|---|
| EP | 0 103 664 B1 | 12/1982 |
| EP | 0 880 940 A2 | 12/1998 |
| EP | 933096 | 8/1999 |
| EP | 1116476 | 7/2001 |
| GB | 1 494 324 A | 12/1977 |
| JP | 2001-212231 | 8/2001 |
| JP | 2005-087520 | 4/2005 |
| WO | WO 99/27863 | 12/1998 |
| WO | WO 99/46005 A | 9/1999 |
| WO | WO 00/60711 | 12/2000 |
| WO | WO 00/72771 A1 | 12/2000 |
| WO | WO 2004/004803 | 1/2004 |

OTHER PUBLICATIONS

"The Physiology Coloring Book", W. Kapit et al., Harper Collins Publishers, 1987, pp. 88-89.

* cited by examiner

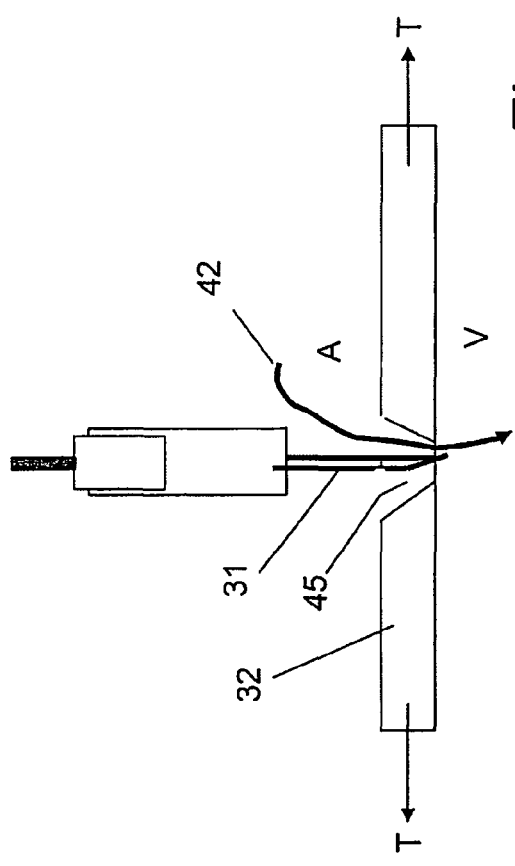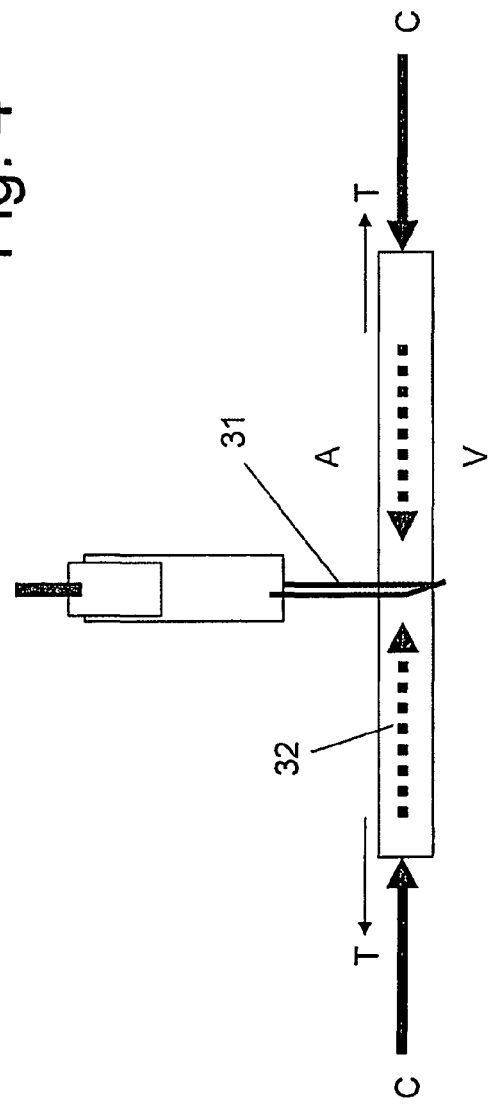

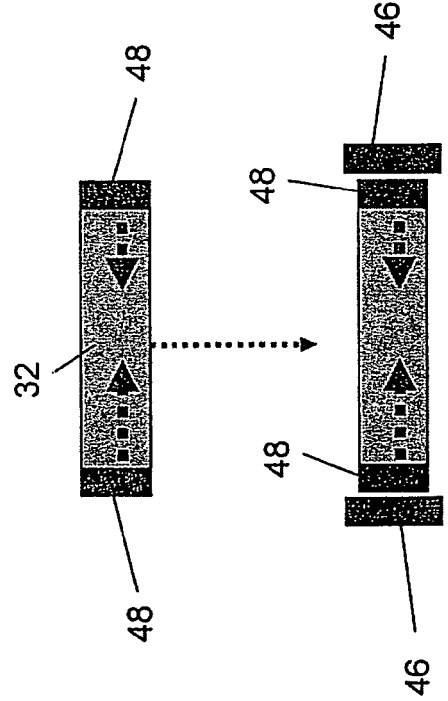

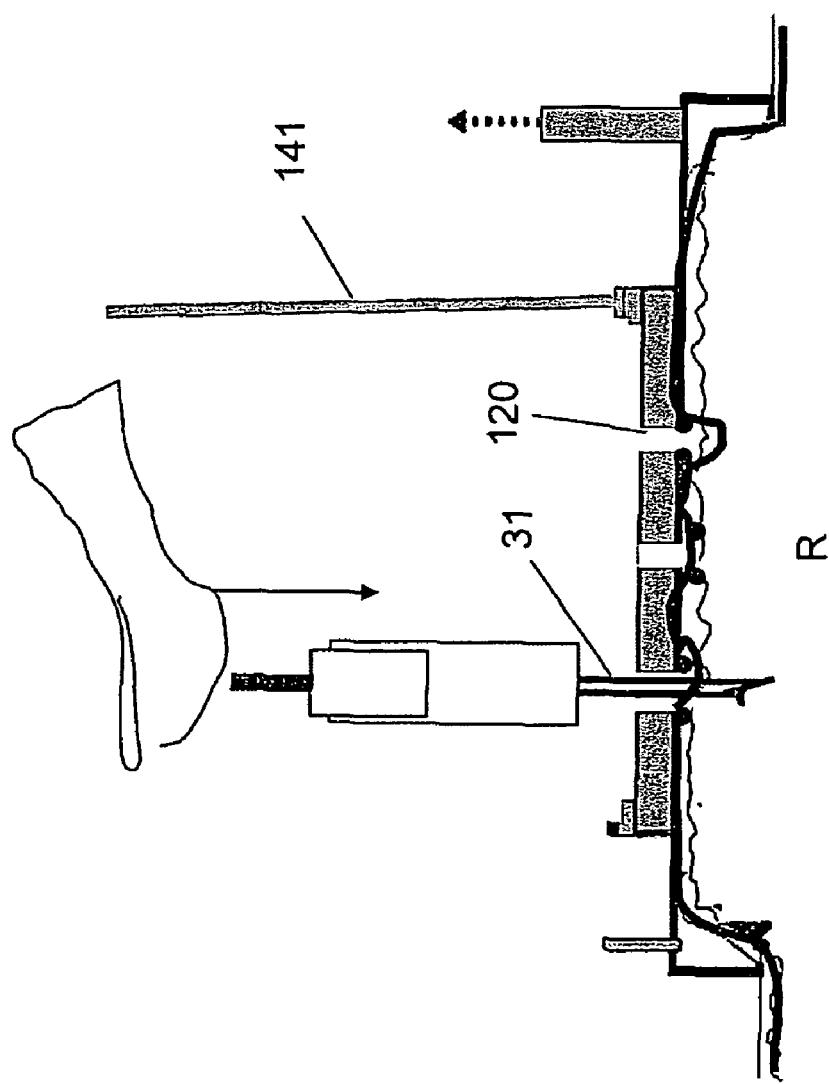

APPARATUS AND METHOD FOR INHIBITING PAIN SIGNALS TRANSMITTED DURING A SKIN RELATED MEDICAL TREATMENT

This application claims priority from IL Patent Application No. 170132 (filed Aug. 4, 2005), now abandoned, IL Patent Application No. 174847 (filed Apr. 6, 2006), and IL Patent Application No. 175486 (filed May 8, 2006), and is a Continuation-In-Part of the U.S. patent application Ser. No. 11/401,674 (filed Apr. 11, 2006), which claims priority from EP Patent Application No. 050007952.4 (filed Apr. 12, 2005) is a Continuation-In-Part of U.S. patent application Ser. No. 11/057,542 (filed Feb. 14, 2005), which claims priority from Israeli Patent Application No. 160510 (filed on Feb. 22, 2004) and is a Continuation-In-Part of U.S. patent application Ser. No. 10/498,382 (filed Jun. 10, 2004), which is a Continuation-In-Part of PCT/IL02/00635 (filed on Aug. 2, 2002), which is derived from IL 147009 (filed on Dec. 10, 2001) and from IL 150094 (filed on Jun. 6, 2002).

FIELD OF INVENTION

The current invention is related to an apparatus adapted to inhibit the sensation of pain during skin treatments in general, and particularly during needle injections, ultrasonic treatments, ultrasonic disruption of tissue, hair removal with a hand held implement, and light based skin treatments.

BACKGROUND OF THE INVENTION

Many medical treatments are accompanied by a pain sensation. The pain sensed within a skin region is generated by pain receptors in the skin. According to the Gate Theory of Afferent Inhibition described in, for example, "The Physiology Coloring Book," W. Kapit et al, Harper Collins Publishers (1987), pages 88-89, the pressure sensed by large, fast-conducting tactile nerves, such as by rubbing the skin, limits the transmission gates in the dorsal horn, excludes access for the weaker pain signal, and therefore inhibits the pain signal transmission by pain nerves in the spinal cord.

The treatment of skin is often very painful and may necessitate the utilization of analgesic topical creams such as EMLA cream produced by AstraZeneca Inc., Canada, or even of anesthetic injections to inhibit the pain. Such pain inhibiting procedures are risky and also increase the total duration of the treatment.

In resent years, ultrasonic treatments of lesions located under the skin have been proposed and performed. By directing ultrasonic waves and the associated mechanical force in the form of vibrations at the lesions, a localized increase in temperature sufficient to treat the lesion is noticeable. This localized increase in temperature also causes a pain sensation. In one ultrasonic treatment, subcutaneous lesions are disrupted with focused ultrasonic waves which generate cavitation in the focal zone, in order to selectively destroy tissue. Examples of ultrasonic cavitation tissue disruptors are a device produced by Ultrashape Ltd., Israel for the reduction of fat and cellulite, which is described in US 2003/0083536 and US 2005/0261584, and a device for the treatment of malignant tissue under the skin produced by GE Medical Systems, USA. The ultrasonic frequency of most treatments is in the 1-10 MHz range, and the focused ultrasonic treatments are generally very painful.

Ultrasonic energy may be used for hair removal, as described in U.S. Pat. No. 6,544,259. Hair removal by means of an ultrasonic device is generally very painful.

Another disruptive treatment which is liable to cause pain is the vibration of hair at a frequency equal to, or slightly greater than, sonic frequency. Disruptive elements are adapted to induce cavitation and disrupt tissue. Cavitation can also be induced under the skin by means of an ultrasonic aspirator.

Another medical treatment that is generally painful is the subcutaneous injection of a medication by means of a needle, causing much apprehension to patients prior to the injection.

U.S. Pat. No. 6,132,392 discloses a pain relieving device for selectively applying three or more pain relieving modalities to an upper body region of a person, including acupressure and at least two other modalities selected from the group of vibration, massage, heat, traction and electric stimulation. The deficiencies of this device with respect to pain inhibition include a low pain reduction, lack of repeatability, and considerable inconvenience to the patient.

US 2002/0013602 discloses a method for reducing the pain associated with an injection or minor surgical procedure at a site on the skin of a patient by urging a skin engaging surface of a pressure member against the skin proximate the site, thereby stimulating the large diameter afferent sensory nerve fibers in the skin proximate the site and at least partially blocking pain signals from the small diameter afferent pain nerve fibers in the skin proximate the site. Some of the disadvantages of this method include the difficulty and inconvenience to apply pressure on skin which is in close proximity to bones, the inability to achieve treatment repeatability, and the difficulty to maintain a constant level of pressure on the skin. Also, while applying external pressure on a skin surface, the pressure receptors are pressed before any pressure is exerted on a deeper neuron extending from the pain receptor. Furthermore, the reactive force applied by bones underlying the pressed skin increases the skin squeezing effect, affecting the compression of blood vessels and of nerves.

It would be desirable to provide a method for alleviating pain during injections or ultrasonic treatments which is more easily carried out and has a greater repeatability than that of the prior art.

US 2004/0254599 discloses a method and apparatus for reducing the perceived pain resulting from the puncturing of skin at a puncture site by generating a sensory distraction, such as vibration, an acoustical signal or an electrical stimulation. One deficiency of this method is that the sensory distraction is generated by means of a relatively complicated mechanism or electronic device. Another deficiency is that a pain inhibiting pressure signal is simulated, and a limited number of pressure sensors, if any, are involved in the pain inhibiting process. A pain signal that is not inhibited by a compressed pressure receptor will therefore be transmitted.

Some prior art devices reduce the level of generated pain by limiting the depth of needle penetration into the skin. WO 2004/004803 discloses an intradermal delivery device comprising a housing including a base deeming a needle aperture, and a skin-engaging surface extending about a periphery of the needle aperture. A syringe of the intradermal delivery device includes a syringe body coupled to the housing and a plunger slidably received within the syringe body. A needle is coupled in fluid communication with the syringe body, and is movable through the needle aperture to penetrate the skin and inject a substance contained within the syringe body therein. A vacuum chamber of the intradermal delivery device is coupled in fluid communication with the base for drawing a vacuum within the base and, in turn, releasably securing the skin-engaging surface to the skin and forming a substantially planar needle penetration region on the skin. The intradermal delivery device further includes at least one stop surface fixed relative to at least a portion of the skin-engaging surface to define a predetermined distance therebetween, and adapted to cooperate with the needle to limit an insertion of the needle into the needle penetration region of the skin. Such a device is incapable of reducing pain when the medical treatment requires a deeper injection depth. Also a downward force is applied to the skin surface.

JP 2001-212231 discloses a device capable of reducing the sensed pain at the time of penetration of a syringe needle. As the housing portion of the device is pressed onto the epidermis of a patient, the air within a variable volume chamber is released. When the syringe needle is introduced into the skin through a suitable aperture of the device, the force applied onto the epidermis as a result of the pressure differential between atmospheric air and that of the chamber helps to disperse the sensed pain during penetration of the syringe needle into the skin. Only the walls of the variable volume chamber having a very small projected surface area contact the drawn skin, and therefore the pain reduction that may be realized with this device is very limited. Also, the vacuum level that is generated by downwardly pressing the housing portion onto the epidermis is very low, and is not sufficient to reduce the sensed pain to a significant extent.

JP 2005-087520 discloses a liquid medicine injector that causes a reduced sensation of pain as a skin region is punctured. A plurality of hollow needles communicate with a liquid medicine container and project outwardly therefrom. A leaf spring provides the driving force for percutaneously injecting the liquid medicine via a needle, and a suction port sucks the air in a recessed part of the container, from which the needles project. In order to reduce pain, a dedicated injector that is compatible with the configuration of the apparatus must be employed. Also, the Gate Theory of Afferent Inhibition is not mentioned in this publication, and therefore a threshold size and threshold vacuum level for achieving pain reduction is not suggested. Furthermore, the sole purpose of generating the vacuum is not to reduce pain, but also to prevent the needle from coming off from the skin in order to ensure precise penetration into the skin at a desired location and depth.

It is an object of the present invention to provide a method and apparatus for inhibiting the resulting pain which is usually sensed during a skin-related medical treatment, such as an ultrasonic treatment of the skin or during an injection into the skin, without use of an analgesic topical cream or anesthetic injection.

It is an object of the present invention to provide a method and apparatus for achieving a large level of pain reduction during a skin-related medical treatment.

It is an additional object of the present invention to provide a method and apparatus for increasing the level of pain reduction during a skin-related medical treatment with respect to prior art vacuum-assisted pain inhibiting apparatus.

It is an additional object of the present invention to provide a method and apparatus for performing painless skin-related medical treatments of high repeatability.

It is yet an additional object of the present invention to provide apparatus having a threshold size and generating a threshold vacuum level, in order to achieve a desired level of pain reduction.

It is yet an additional object of the present invention to provide apparatus that is suitable for inhibiting the transmission of pain signals in the dorsal horn by generating pressure signals in a sufficiently high number of pressure receptors in the skin.

It is yet an additional object of the present invention to provide a method and apparatus for performing painless injections with any commercially available injector.

SUMMARY OF THE INVENTION

The present invention provides an apparatus which inhibits pain signals generated by pain receptors in the skin during a skin related medical treatment from being transmitted to the brain by inducing a controlled compression of a skin region, comprising:

a) an evacuation chamber comprising an essentially rigid interface element through which a medical treatment can be administered to a selected skin region, one or more walls which are placeable on, or in the vicinity of, said skin region, an interior defined by at least said one or more walls and by said interface element, and an opening at the bottom of said interior which is sealable by said skin region;

b) means for generating a vacuum within said evacuation chamber interior, the level of the applied vacuum suitable for drawing said skin region through said opening towards, and in a compressing relation against, said interface element, whereby to inhibit the transmission of a pain signal generated by pain receptors located within said skin region; and c) means for administering a skin related medical treatment, said administering means adapted to pass through said interface element and to be directed to said compressed and pain inhibiting skin region.

As referred to herein, the "interface element" is an element through the thickness of which the administering means can pass, yet is suitable for sufficiently secluding the evacuation chamber interior from the evacuation chamber exterior in order to achieve said vacuum level being suitable for inhibiting the transmission of pain signals.

As referred to herein, a "medical treatment" is a procedure administered to a living subject to improve a pathological disorder, to improve the appearance of a skin region, to effect a change in tissue, to introduce beneficial material into the body, and a dental or oral procedure such as making a small incision in the gums.

The administering means may be an injection needle, and the corresponding interface element is puncturable thereby or is provided with a plurality of apertures through each of which the injection needle may introduced.

The administering means may also be electromagnetic energy, such as ultrasonic waves, laser light, and IPL light, and the corresponding interface element is transparent or translucent to said electromagnetic energy.

As referred to herein, a "vacuum level" is the absolute pressure below atmospheric pressure. A vacuum level of 500 mmHg is therefore a pressure of 500 mmHg below atmospheric pressure. When a vacuum level is referred to as being greater than a given value, e.g. greater than 400 mmHg, the pressure within the evacuation chamber interior is an absolute pressure of a value below atmospheric pressure greater than said given value.

Preferably, the surface area of the interface element is greater than a threshold surface area, e.g. at least 100 mm$^2$, which is suitable for inhibiting the transmission of a pain signal generated by pain receptors located within the skin region.

Preferably, the vacuum level within the evacuation chamber is greater than a threshold vacuum level, e.g. at least 150 mmHg and preferably at least 400 mmHg, which is suitable for inhibiting the transmission of a pain signal generated by pain receptors located within the skin region.

In one aspect, the vacuum generating means comprises a vacuum pump, such as a dual air-gel vacuum pump, in fluid communication with the evacuation chamber.

In one aspect, the vacuum generating means is a vacuum source, such as a pre-evacuated container, in fluid communication with the evacuation chamber and means for isolating said vacuum source from the evacuation chamber interior. As referred to herein, a "vacuum source" is a member which is in communication with the evacuation chamber and is subjected to a sufficiently high vacuum to draw the skin region in compressing fashion against the interface element.

The volume of the vacuum source is preferably at least twice the volume of the evacuation chamber.

The isolation means may be a valve or a breakable stop, and may be openable by control means. The control means is preferably a controller and a skin contact detector in communication with said controller for sensing the placement of the evacuation chamber onto the skin region, said controller adapted to generate a signal for opening the isolation means following placement of the evacuation chamber onto the skin region.

In one aspect, the pre-evacuated container is integrally connected to the evacuation chamber.

A control means for synchronizing the activation of the vacuum generating means is preferably employed.

In one aspect, the control means is a mechanical control means, such as a pin placeable on the skin region, the pointed end of said pin adapted to pierce a membrane stretched across the interior of a conduit extending between the pre-evacuated container and the evacuation chamber once the evacuation chamber is placed on the skin region.

The control means may further comprise a valve in communication with both the conduit and surrounding ambient air, said valve being openable whereby to release the vacuum by kinematic means a predetermined period of time following placement of the evacuation chamber on the skin region.

In one aspect, the control means comprises a controller and a skin contact detector in communication with said controller for sensing the placement of the evacuation chamber onto the skin region, said controller adapted to generate a first signal for activating the vacuum generating means following placement of the evacuation chamber onto the skin region and to generate a second signal for deactivating the vacuum generating means a predetermined duration, e.g. no longer than approximately 6 seconds following generation of said first signal. The skin contact detector may be an opto-coupler or a microswitch.

The control means may further comprise a pressure sensor in fluid communication with the interior of the evacuation chamber and in electrical communication with the controller, the controller being further adapted to control the operation of the vacuum generating means so that a predetermined pain inhibiting vacuum level ranging between 400 mmHg and 1 atmosphere will be generated within the evacuation chamber.

In one aspect, the vacuum generating means comprises at least one control valve, the controller being suitable for delivering air through said at least one control valve in order to increase the pressure in the evacuation chamber to atmospheric pressure following the generation of the second signal, to allow for effortless repositioning of the evacuation chamber to a second skin region, the control means being selected from the group of electronic means, pneumatic means, electrical means, and optical means.

In one aspect, the interface element is pre-compressed.

In one aspect, the interface element is planar and may be retained in a cover element attached to one or more sidewalls.

In one aspect, the interface element is curvilinear and may be retained by one or more sidewalls.

The apparatus is suitable for the painless administration of medical treatments selected from the group of ultrasonic-based hair removal, ultrasonic-based collagen tightening, ultrasonic-based blood vessel sealing, ultrasonic-based treatment of fatty or cellulite tissue, injections for vaccines, injections for the administration of drugs, injection of collagen, mesotherapy, removal of hair with a hand held implement, needle epilation, injection of collagen within the epidermis, tattoo removal, and the treatment of pigmented lesions.

In one embodiment, the means for administering the medical treatment is an injection needle.

In one aspect, the interface element is puncturable, and may be a subdivided interface element.

In one aspect, the interface element is an apertured interface element, an injection needle being introducible through each of said apertures. The total area of the apertures is less than 20% of the total area of the interface element.

In one aspect, the apertures are covered by a shield element. The shield element may be placed directly on top of the interface element, or alternatively, a seal element may be interposed between the shield element and the interface element. Marks corresponding to the location of the apertures are preferably indicated on the upper face of the shield.

In one aspect, the apparatus further comprises means for maintaining the vacuum within the evacuation chamber following termination of the vacuum generating means.

In one aspect, the vacuum maintaining means comprises a plurality of rims connected to the underside of the apertured interface element, each of said rims encircling a corresponding aperture formed in the interface element and adapted to produce a volume of negative pressure within the evacuation chamber for drawing the skin region in compressing relation against the interface element following termination of the vacuum generating means, said volume being enclosed by the interface element, rim, and drawn skin region or being enclosed by the interface element, evacuation chamber sidewall, and drawn skin region, In one aspect, the apparatus further comprises means for guiding the injection needle through an aperture to the drawn skin region.

In one aspect, the apparatus further comprises means for administering a plurality of injection needles, such as a bar for holding a plurality of needle applicators therebelow and a guide track substantially perpendicular to said bar.

In one aspect, an evacuation chamber sidewall is an interface element.

In one aspect, the evacuation chamber is configured as a slit defined by elongated, planar sidewalls and by a rigid upper surface extending between, and having a considerably shorter length than, said sidewalls.

In one aspect, the apparatus further comprises a vibrator kinematically connected to the interface element.

In one embodiment, the means for administering the medical treatment is a beam of ultrasonic waves and the interface element is made of a material which is transparent to ultrasonic waves. The ultrasonic waves preferably have a frequency ranging from 1 to 10 MHz and are generated by means of an ultrasonic transducer.

In one embodiment, an apparatus is provided for alleviating or preventing pain caused by a treatment with electromagnetic energy of a targeted skin structure, comprising:

a) an element subjected to a generated vacuum therebelow, the level of the generated vacuum being sufficiently high to draw a skin target underlying said element towards, and in a compressing relation against, said element, whereby to alleviate or prevent the transmission of a pain signal generated by pain receptors located within said skin target; and b) a pulsed source of electromagnetic energy for generating waves that are transmitted through said element and that are suitable for treating a skin disorder within said skin target.

In one aspect, the electromagnetic energy is laser or IPL light having a wavelength ranging from 400 to 1800 nm.

In one aspect, the element which is subjected to a generated vacuum therebelow is an interface element of an evacuation chamber, said evacuation chamber further comprising one or more walls which are placeable on, or in the vicinity of, said skin region, an interior defined by at least said one or more walls and by said interface element, and an opening at the bottom of said interior which is sealable by the skin target.

In one aspect, each wall of the evacuation chamber is puncturable, a darkened needle capable of piercing a wall of the evacuation chamber, attracting the optical energy of the light, and thermally damaging the surrounding skin structure.

In one aspect, the light has an energy density ranging from 10 to 100 $J/cm^2$ and a pulse duration ranging from 10 to 300 millisec.

In one aspect, the apparatus further comprises gliding apparatus for displacing a light source distal end over the interface element at a speed ranging from 0.3 to 40 cm/sec.

In one aspect, the light source distal end is displaced by means of an optical detector that senses the presence of a marker on the interface element.

In one aspect, the light source distal end is displaced by means of a texture sensing mechanism.

In one aspect, the interface element is an apertured interface element, the light propagating through each of the apertures without being transmitted through the material from which the interface element is composed. The light may be generated by a $CO_2$ or Erbium laser.

The present invention is also directed to a method for inhibiting pain signals generated by pain receptors in the skin during a skin related medical treatment, comprising the steps of:

a) positioning a rigid interface element above a selected skin region;

b) applying a vacuum of a sufficient value over said skin region such that the latter is flattened and compressed against said interface element; and c) administering a skin related medical treatment by means adapted to pass through said interface element and to be directed to said compressed skin target, whereby pain signals generated by the nervous system during said medical treatment are inhibited due to the contact of said skin region onto said interface element.

The surface area of the interface element is preferably greater than a threshold surface area suitable for inhibiting the transmission of a pain signal generated by pain receptors located within the skin region, e.g. least 100 $mm^2$.

The vacuum level within the evacuation chamber is greater than a threshold vacuum level suitable for inhibiting the transmission of a pain signal generated by pain receptors located within the skin region, e.g. at least 150 mmHg and preferably at least 400 mmHg.

The medical treatment is selected from the group of ultrasonic-based hair removal, ultrasonic-based collagen tightening, ultrasonic-based blood vessel sealing, ultrasonic-based treatment of fatty or cellulite tissue, injections for vaccines, injections for the administration of drugs, injection of collagen, mesotherapy, removal of hair with a hand held implement, needle epilation, injection of collagen within the epidermis, tattoo removal, the treatment of pigmented lesions, and making a small incision in the gums.

The duration of the applied vacuum preferably ranges from 0.1 to 6 seconds.

BRIEF DESCRIPTION OF THE DRAWINGS

In the drawings:

FIG. 4 schematically illustrates the tensile forces to which an interface element is normally subjected as a vacuum is applied to an evacuation chamber;

FIG. 5 schematically illustrates the factory-induced compressive forces that counteract the tensile forces of FIG. 4;

FIGS. 6*a-e* schematically the generation of factory-induced compressive forces by press fitting an interface element in a retaining member;

FIGS. 14*a-b* illustrate an apertured interface element having a shield element, wherein FIG. 14*a* illustrates the shield element as it is covering the interface element and FIG. 14*b* illustrates the interface element after the shield element has been removed therefrom;

FIGS. 20a-b schematically illustrate an apparatus according to one embodiment of the invention which does not require a vacuum pump for administering repeated painless injections by a single medical professional wherein FIG. 20a illustrates the positioning of the evacuation chamber before the application of vacuum therein and FIG. 20b illustrates the administration of an injection after a skin region is drawn by the vacuum applied to the evacuation chamber;

DESCRIPTION OF PREFERRED EMBODIMENTS

Figure 1:
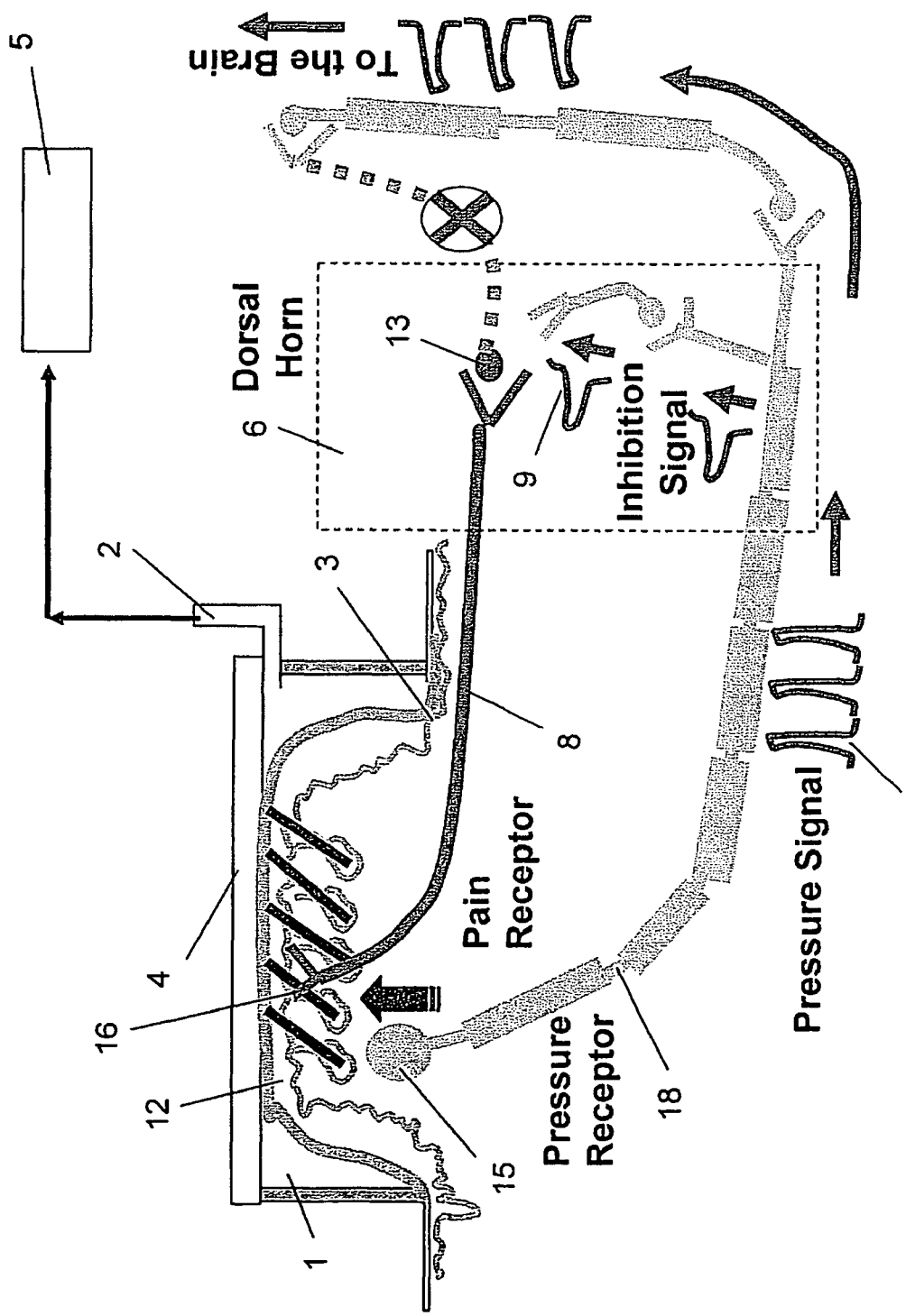
FIG. 1 schematically illustrates a portion of the nervous system that is involved in the generation of a pain inhibiting signal as a skin region is flattened following the application of a suitable vacuum level thereto.

The present invention relates to apparatus adapted to alleviate or prevent the normal pain which is sensed during a skin-related medical treatment, such as an ultrasonic treatment of the skin or during an injection into the skin. The apparatus of the present invention includes an evacuation chamber having a rigid surface overlying an aperture formed in a skin engaging lower portion. When the evacuation chamber is placed on a selected skin region and a vacuum of a sufficiently high level is applied to the skin region, the skin region is drawn through the aperture towards, and is compressed against, the rigid surface. The rigid surface may extend from the upper edge of the evacuation chamber walls or may be retained within a cover element connected to, or integrally formed with, the evacuation chamber walls. Due to the compression of the skin against the rigid surface, pain signals generated by pain receptors located within the skin region during a medical treatment of the skin are alleviated or prevented.

Medical treatments that have been heretofore painful to patients may be administered in a painless fashion with the use of the apparatus of the present invention. Typical medical treatments that may be administered in painless fashion are ultrasonic-based hair removal, ultrasonic-based collagen tightening, ultrasonic-based blood vessel sealing, ultrasonic-based treatment of fatty or cellulite tissue, injections for vaccines, injections for the administration of drugs, injection of collagen, mesotherapy, removal of hair with a hand held implement, and needle epilation.

Needle epilation, which is carried out by inserting a needle into the skin along a hair shaft to a depth of a few millimeters, may be performed with use of the apparatus of the present invention without causing pain to the patient. The duration of this procedure is approximately one second, including the time needed to insert the needle and to destroy a single hair follicle. While the procedure is very effective in terms of heating the follicle by means of the needle and destroying the critical organs necessary for hair regeneration and growth by applying an electrical current, it is very painful. By applying a vacuum and inducing compression of the drawn skin region against a rigid surface of the evacuation chamber, the pain sensation is inhibited while efficacious hair destruction is maintained. The apparatus of the present invention will also facilitate painless hair removal at skin regions, such as the face, particularly for women suffering from an excess in androgenic hormones, for which laser or IPL light, i.e. photepilation, is not suitable. Another advantage of the apparatus of the present invention is that thin and white hairs, which cannot be removed by photoepilation, will be able to be removed by needle epilation in painless fashion.

To determine operability of the apparatus of the present invention, the degree of vacuum-assisted pain alleviation was evaluated according to a modified McGill pain questionnaire. The McGill pain questionnaire is well known to pain specialists, and is described by R. Melzack, "The McGill Pain Questionnaire: Major Properties and Scoring Methods," Pain 1 (1975), pp. 277-299. The sensed pain associated with 45 skin targets following a light-based treatment, i.e. by means of laser or IPL light, of vacuum-induced flattened skin was compared to the pain associated with light-based treatments conducted without skin flattening. A dramatic pain reduction, from an average of pain level 4, which is indicative of a very painful treatment, to an average of pain level 2, which is indicative of a lack of pain, was revealed.

The inventors have found that an applied vacuum level of at least 150-200 mmHg, and preferably at least 400 mmHg, is generally needed to alleviate pain. A lower vacuum level, such as of 50-100 mmHg, has been found to be not sufficient for the alleviation of pain.

It will be appreciated that the Gate Theory of Afferent Inhibition, which states that a pressure signal sensed by large, fast-conducting tactile nerves excludes access for the weaker pain signal and therefore inhibits the pain signal transmission by pain nerves in the spinal cord, has been established only during the application of an external positive pressure to the skin region. The Gate Theory of Afferent Inhibition has never been evaluated heretofore with respect to the application of a negative pressure to the skin region, whereby internal upward pressure-derived forces are generated within the skin and may affect the pain signal transmission in different ways.

It will be appreciated that the application of a suitable vacuum over a skin region which causes the latter to be flattened by an overlying rigid surface is physiologically not equivalent to the application of positive pressure over the skin.

Applying a positive pressure onto a skin surface compresses and squeezes the same. Bones located under the skin surface apply a reactive force and therefore increase the degree of skin compression, as well as to the squeezing of blood vessels and of nerves bundles. The physiological reaction to the pressing of skin depends on the skin thickness, and particularly, on the distance of the bones from the skin surface.

In contrast, bones underlying a skin surface drawn by a vacuum applied thereto are not influential during a skin flattening procedure. Since the underlying bones do not apply a reactive force as the connective tissue overlying these bones is drawn towards the vacuum chamber, the degree to which blood vessels and nerve bundles within a drawn skin region are compressed is reduced. Thus the physiological processes of connective tissue associated with a vacuum induced skin flattening procedure are different than those of connective tissue which is compressed as a result of the application of positive pressure thereto. The inventors are not aware of any published clinical studies which describe the effects of a vacuum induced skin flattening procedure. Any clinical results of a study regarding the application of positive pressure over a skin surface are not expected to be clinically relevant to those obtainable with respect to a vacuum induced skin flattening procedure.

The generation of a vacuum to a skin region may be advantageously controlled, in order to ensure that the skin region will be flattened prior to the medical treatment and to achieve a predetermined rate of repeatability.

The inventors have surprisingly found that a contributory factor to the level of vacuum-assisted pain reduction is the surface area of the rigid surface. Without wishing to be limited by any particular theory, the inventors believe that the relationship between the level of vacuum-assisted pain reduction and the surface area of the rigid surface is reflected in FIG. 1. As schematically illustrated, evacuation chamber 1 is shown to be placed above skin region 12, which has been selected as the target of a normally painful skin-related medical treatment. The air in evacuation chamber 1 is evacuated by means of a vacuum pump 5 via conduit 2 in communication with vacuum chamber 1. Following application of the vacuum within evacuation chamber 1, skin region 12 is upwardly drawn within the interior of evacuation chamber 1, contacts planar rigid surface 4, and is flattened thereby. A rigid surface 4 of evacuation chamber 1 having a sufficiently large area ensures that a correspondingly large number of pressure receptors 15 will be compressed. Pressure receptors 15 sense the compression of skin region 12 as it is flattened by rigid surface 4, and fast conducting myelinated pressure nerve 18 located within skin region 12 transmits a generated pressure signal 17 to dorsal horn 6 of the spinal cord.

Pressure signal 17 functions as an inhibition signal 9 within dorsal horn 6 at a synaptic connection 13 to the brain, thereby inhibiting the pain signal, which is normally transmitted to the brain via the spinal cord through slower non-myelinated pain nerve 8 after being sensed by pain receptor 16 as a result of a pain generating medical treatment, from being transmitted to the brain. The inhibition of the transmission of pain signal impulses to the brain by pressure signals 17 is of chemical origin. Once inhibition signal 9 reaches synaptic connection 13, a negative charge is generated which inhibits the activation of the pain nerve which is in communication with the brain.

If the area of rigid surface 4 is not sufficiently large, fewer pressure receptors 15 will be compressed and a pain sensation will be felt due to the transmission of the corresponding pain signal to the brain from pain nerves which are not gated by pressure receptors. Pain reduction has been found to be noticeable in skin regions such as the back, hands, legs and armpits when the rigid surface has an area greater than at least 100 mm$^2$, such as one that has a length of 20 mm and a width of 40 mm.

The inventors have also surprisingly found that the pain signals cease to be inhibited when the duration of the applied vacuum is longer than a predetermined value. When the duration of the applied vacuum is longer than approximately 6 seconds, depending on the vacuum level and the surface area of the rigid surface against which the skin region is compressed, the compression of the drawn skin against the rigid surface does not provide a pain inhibiting effect. A medical treatment administered to skin region 12 is liable to very painful if a pain inhibition signal is not generated during the treatment, e.g. when the evacuation chamber, if one exists, is not suitable for drawing skin in compressing fashion against the rigid surface, or the vacuum applying duration is longer than approximately 6 seconds and the delay between the generation of the vacuum and the medical treatment administered to the skin target is significantly greater than 6 seconds. The maximum vacuum applying duration that provides a pain inhibiting effect may change depending on the individual patient and the location of the bodily part to which the medical treatment is administered.

The inventors have also surprisingly found that the pain signals continue to be inhibited for approximately 2-3 seconds after release of the vacuum. Since the pain inhibition effect continues after release of the vacuum, a painless injection may be administered immediately after the vacuum is released and the evacuation chamber or a portion thereof is removed from the target skin region. Such a procedure is advantageous for those skin compression conditions which prevent a sufficient amount of injection material to be introduced into the skin. Despite the relative large volume of beneficial material that is introduced into a skin region during an injection, eg. 1 cm$^3$, the inventors have surprisingly found that the presence of such beneficial material within the epidermis and dermis as it is being absorbed within the body does not cause any discomfiture as a result of the pain inhibition. The inventors have also surprisingly found that the beneficial material that is intradermally injected is not rejected from the body despite the increased volume of the skin region as the vacuum is applied.

Figure 2:
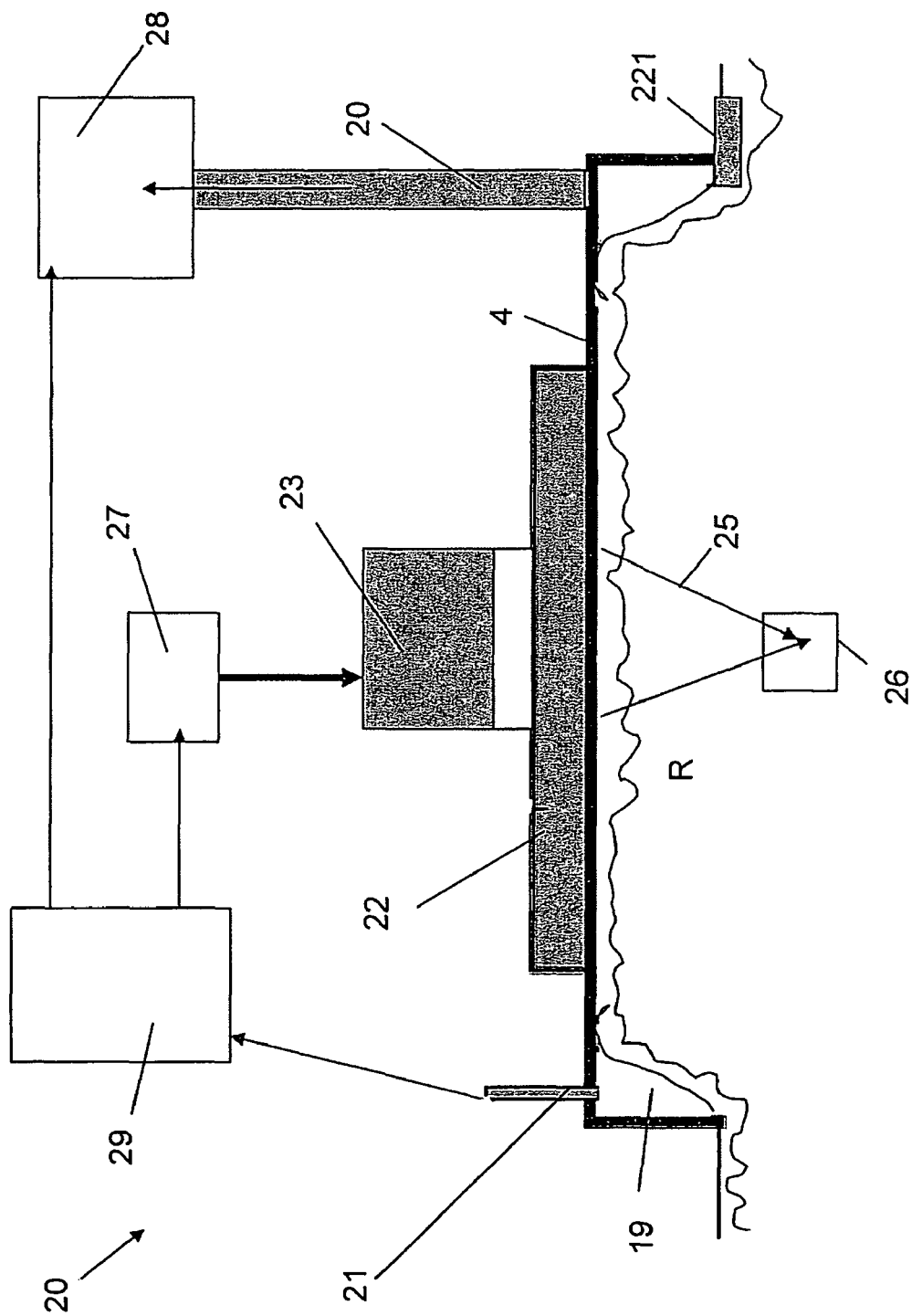
FIG. 2 schematically illustrates apparatus that is suitable for inhibiting pain during an ultrasound-based medical treatment.

FIG. 2 schematically illustrates an embodiment of the present invention which is suitable for alleviating pain caused by a skin-related ultrasonic treatment. The apparatus, which is generally indicated by numeral 20, comprises evacuation chamber 19 placed on a skin region R, planar rigid surface 4 of evacuation chamber 19 overlying skin region R, interface element 22 placed on, or connected to, rigid surface 4 through which ultrasonic waves propagate before impinging upon the drawn skin region R, vacuum pump 28, and electronic control unit 29. Evacuation chamber 19 may have a height of 7 mm and an area of 20×40 mm, although an evacuation chamber area of 20×50 mm, 12×12 mm, 12×50 mm, 20×50 mm, or any other suitable pain inhibiting dimension is acceptable. Interface element 22, which is made of a material which is transparent to ultrasonic waves, e.g. polyethylene having a thickness of 2 mm, thick rubber, or thick silicon, is sufficiently rigid to prevent surface 4 from flexing as skin region R is compressed thereagainst, thereby increasing the degree of skin compression and the corresponding degree of pain inhibition.

The ultrasonic waves having a frequency ranging from 1-10 MHz are generated by means of ultrasonic transducer 23, e.g. made from PZT and dimensioned with a length of 20 mm. Ultrasonic transducer 23, which is suitable for treating subcutaneous target 26, such as malignant and non-malignant lesions, fatty tissue, cellulite tissue, a blood vessel or a hair follicle, can be configured as a concave reflector such as produced by Ultrashape Ltd., Israel, which is suitable for emitting a focused beam 25 impinging upon target 26. Alternatively, focusing may be achieved by a phased array technique. Transducer 23 is activated by electronic power supply 27, e.g. produced by General Electric.

Vacuum pump 28, which is adapted to evacuate the interior of evacuation chamber 19 via conduit 20, is activated by means of skin contact sensor 221, e.g. an opto-coupler or a microswitch well known to those skilled in the art. Skin contact sensor 221 is in electrical communication with electronic control unit 29 and is adapted to detect the placement of evacuation chamber 19 in the vicinity of skin region R. Vacuum pump 28 may be driven by an inexpensive DC motor or an AC motor. Alternatively, vacuum pump 28 may be a dual air-gel vacuum pump described in copending U.S. patent application Ser. Nos. 11/057,542 and 11/401,674 by the same applicant, the description of which is incorporated herein by reference, when skin region R is coated by gel.

A pressure sensor 21 in communication with the interior of evacuation chamber 19 is capable of detecting the generated vacuum level therewithin, to ensure that vacuum pump 28 will automatically generate a predetermined pain inhibiting vacuum level ranging between 400 mmHg and 1 atmosphere.

Pressure sensor 21 transmits a signal indicative of the generated vacuum level to electronic control unit 29, which controls both vacuum pump 28 and power supply 27 of ultrasonic transducer 23.

Electronic unit 29 therefore controls apparatus 20 according to the following sequence. After skin contact sensor 221 detects the placement of evacuation chamber 19 on a skin surface in the vicinity of skin region R, vacuum pump 28 is activated in order to apply a suitable pain inhibiting vacuum level within evacuation chamber 19, as detected by pressure sensor 21. Following generation of the pain inhibiting vacuum level, which is generally achieved within less than 0.5 second, power supply 27 of ultrasonic transducer 23 is activated by power supply 27 to commence the medical treatment directed at target 26. Power supply 27 is then deactivated in order to terminate the medical treatment after a predetermined duration, e.g. 1.5 sec, corresponding to a treatment duration of 1 sec and a delay thereafter of 0.5 sec. Vacuum pump 28, or an additional pump which is not shown, is then commanded to release the vacuum within evacuation chamber 19.

Figure 3:
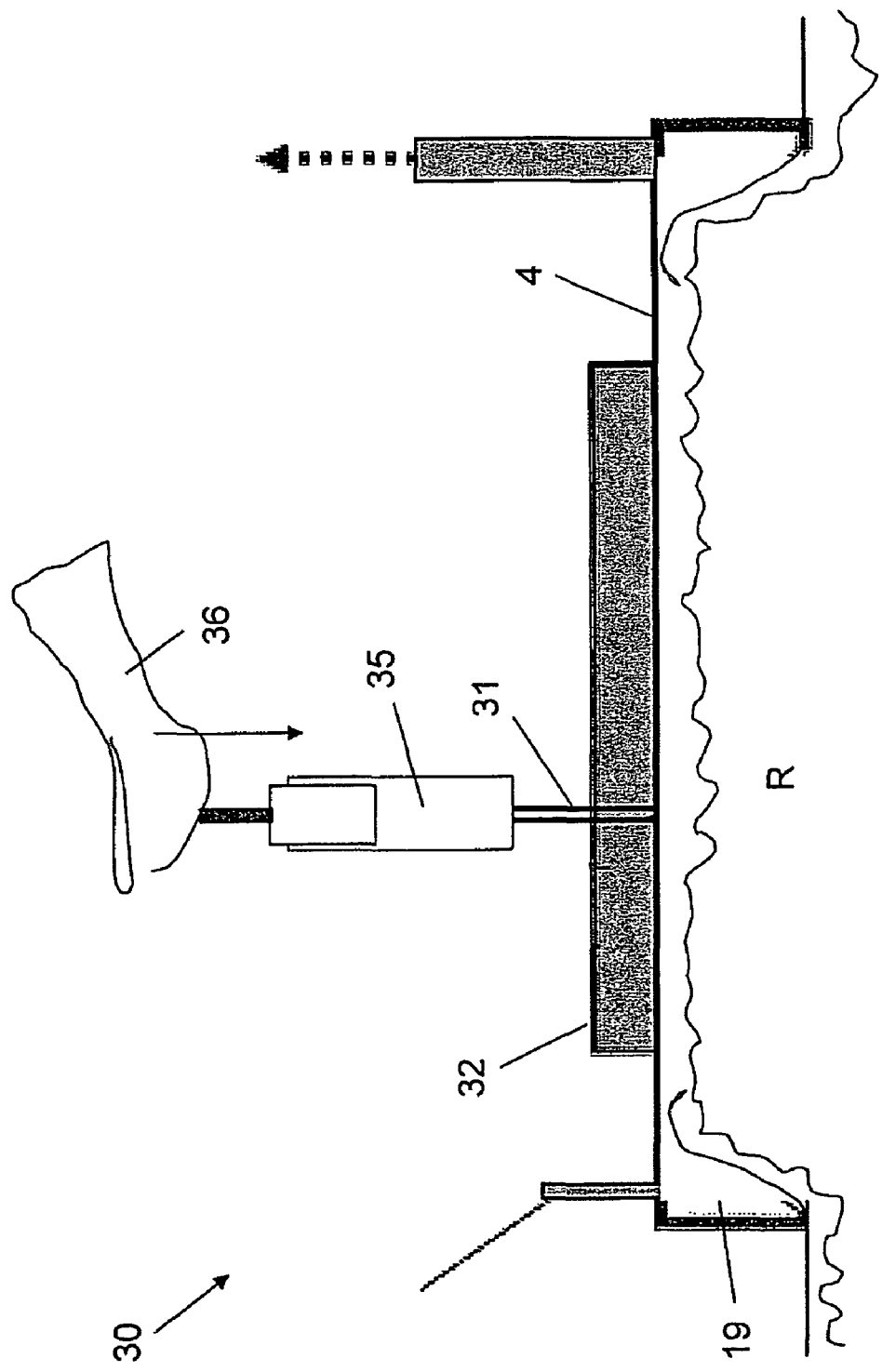
FIG. 3 schematically illustrates an evacuation chamber and the corresponding interface element that are suitable for inhibiting pain during an injection into a target skin region, according to one embodiment of the invention.

FIG. 3 schematically illustrates an embodiment of the present invention which is suitable for ensuring painless injections. With the exception of interface element 32, apparatus 30 is similar to apparatus 20 of FIG. 2. As a vacuum is applied to evacuation chamber 19, skin region R is flattened by rigid surface 4. The application of the vacuum allows skin region R to be drawn towards, and compressed by, rigid surface 4, thereby alleviating the immediate sharp pain which is normally sensed during the injection of needle 31 and enabling a larger skin volume to accept the injected material. Rigid surface 4 and interface element 32 are made of a puncturable material, so that when needle applicator 35 is depressed by the finger 36 of a health professional, needle 31 is downwardly displaced, penetrating interface element 32, rigid surface 4, and skin region R. Interface element 32 is preferably dimensioned to optimize the level of pain inhibition.

As shown in FIG. 4, interface element 32 is normally subjected to tensile forces T after being punctured by needle 31 if any of the measures which will be described hereinafter are not taken. Due to the pressure differential between ambient pressure side A and vacuum side V of interface element 32, stream of air 42 flows through puncture site 45, acting on the surrounding walls of the puncture site and causing the puncture site to be enlarged as a result of the influence of tensile forces T which pull interface element 32 to the periphery of the evacuation chamber. Over the course of time, interface element 32 is liable to tear and the vacuum level within the evacuation chamber is liable to be drastically reduced due to the passage of air through puncture site 45.

To counteract the effect of the tensile forces, interface element 32 may be factory-produced under compression. As shown in FIG. 5, compressive forces C directed towards the center of interface element 32 counteract the tensile forces T that are produced following the penetration of needle 31 into the interface element and the subsequent passage of air through the puncture site due to the pressure differential between ambient pressure side A and vacuum side V of interface element 32. Exemplary suitable puncturable materials that can be easily subjected to factory-produced compressive forces are cork and thin polymeric materials, e.g. silicon having a thickness of 6 mm.

The interface element may be subjected to factory-produced compressive forces by being press fitted in a retaining member smaller than the size of the interface element, as schematically illustrated in FIGS. 6*a-e*. Before being compressed, interface element 32 shown in FIG. 6*a* is longer than retaining member 46 shown in FIG. 6*c*, which is provided with the cover element of the evacuation chamber. Interface element 32 is first elastically compressed, as shown in FIG. 6*b*, into temporary frame 48 defining an interior of smaller dimensions than the interior defined by retaining member 46. Temporary frame 48 is then inserted within retaining member 46, as shown in FIG. 6*c*, and then broken, as shown in FIG. 6*d*. Once temporary frame 48 is broken, interface element 32 slightly expands, abutting retaining member 46, as shown in FIG. 6*e*. Once interface element abuts retaining member 46, its length is shorter than its original dimension shown in FIG. 6*a* and therefore remains in a permanent compressed state.

Figure 7A:
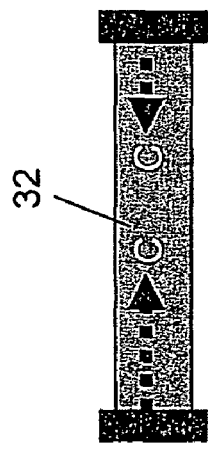
FIG. 7*a* schematically illustrates an interface element that is subjected to compressive forces.
Figure 7B:
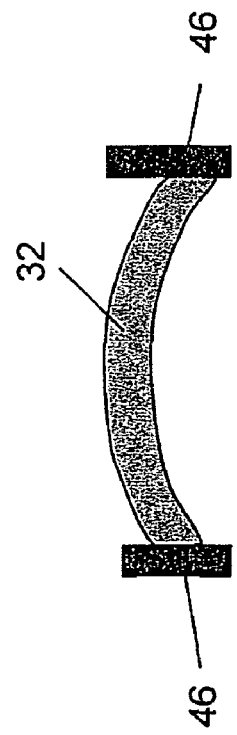
FIG. 7*b* schematically illustrates the aspect ratio of the interface element of FIG. 7*a* after being subjected to compressive forces.
Figure 7C:
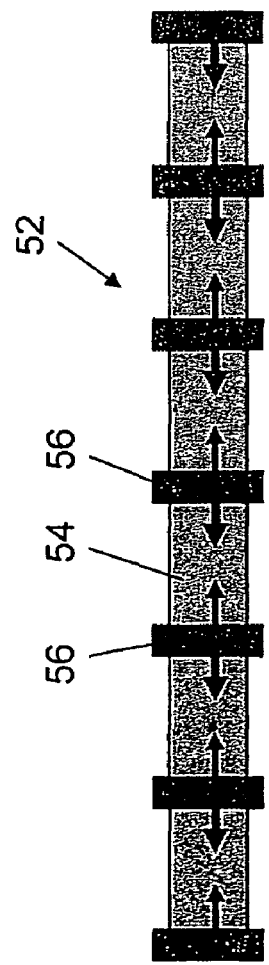
FIG. 7*c* schematically illustrates a subdivided interface element by which the aspect ratio may be reduced.

Due to the compressive forces C to which interface element 32 is subjected, as shown in FIG. 7*a*, the interface element has a tendency to assume a concave shape between its retaining element 46, as shown in FIG. 7*b*. The aspect ratio of interface element 32 is dependent upon the selected interface element material. The aspect ratio may be relatively high when a homogeneous material such as silicon is employed, and is generally low when a heterogeneous material such as cork is employed. Since interface element 32 tends to attain a minimal energy level corresponding to a decompressed state when its aspect ratio is relatively high, the interface element is liable to tear and to be unable to maintain a relatively high vacuum level when punctured by an injection needle, similar to the situation when it is not compressed and tensile forces increase the size of the puncture site, as shown in FIG. 4. To limit the aspect ratio of an interface element made of silicon, which is generally needed to maintain a sterile atmosphere above the target skin region of the medical treatment, a subdivided interface element 52 may be employed, as shown in FIG. 7*c*. Subdivided interface element 52 comprises a plurality of silicon sections 54, each of which is compressed between two dividing walls 56, e.g. made of polycarbonate. The dimensions of each section 54 are preferably small, e.g. 4 mm×4 mm×4 mm, to limit the degree to which each section is bent. During injection, the needle penetrates a silicon section 54. A subdivided interface element is unnecessary when the interface element is made from a heterogeneous material such as cork, melted grains of silicon, or rubber.

Figure 8:
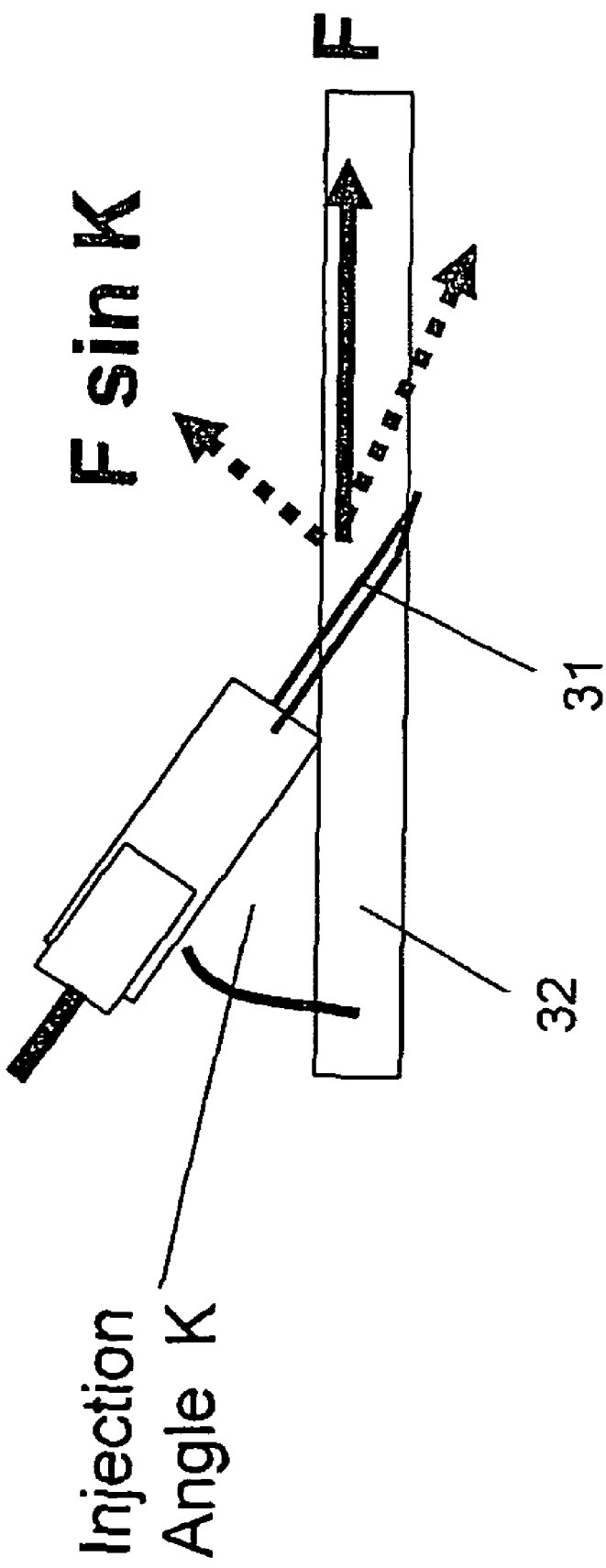
FIG. 8 schematically illustrates the administering of an injection by a small injection angle to thereby increase the tear resistance of the interface element.

To prevent tearing of the interface element, injection needle 31 may be manipulated by the health professional administering the treatment such that it is disposed at a small injection angle K relative to a horizontal interface element 32, as shown in FIG. 8. At a small injection angle of K, the resultant tearing force normal to needle 31 is significantly reduced from F to F sin K, thereby minimizing the risk of structural failure to the interface element. The interface element will not tear when the injection angle is less than a predetermined value, which is dependent upon the strength of the interface material, its elasticity, and its threshold tearing force being a function of the aspect ratio of the interface element. The tear resistance of the interface element is increased when the target skin region is flattened by the interface element and thereby seals the puncture site within the interface element.

Figure 9:
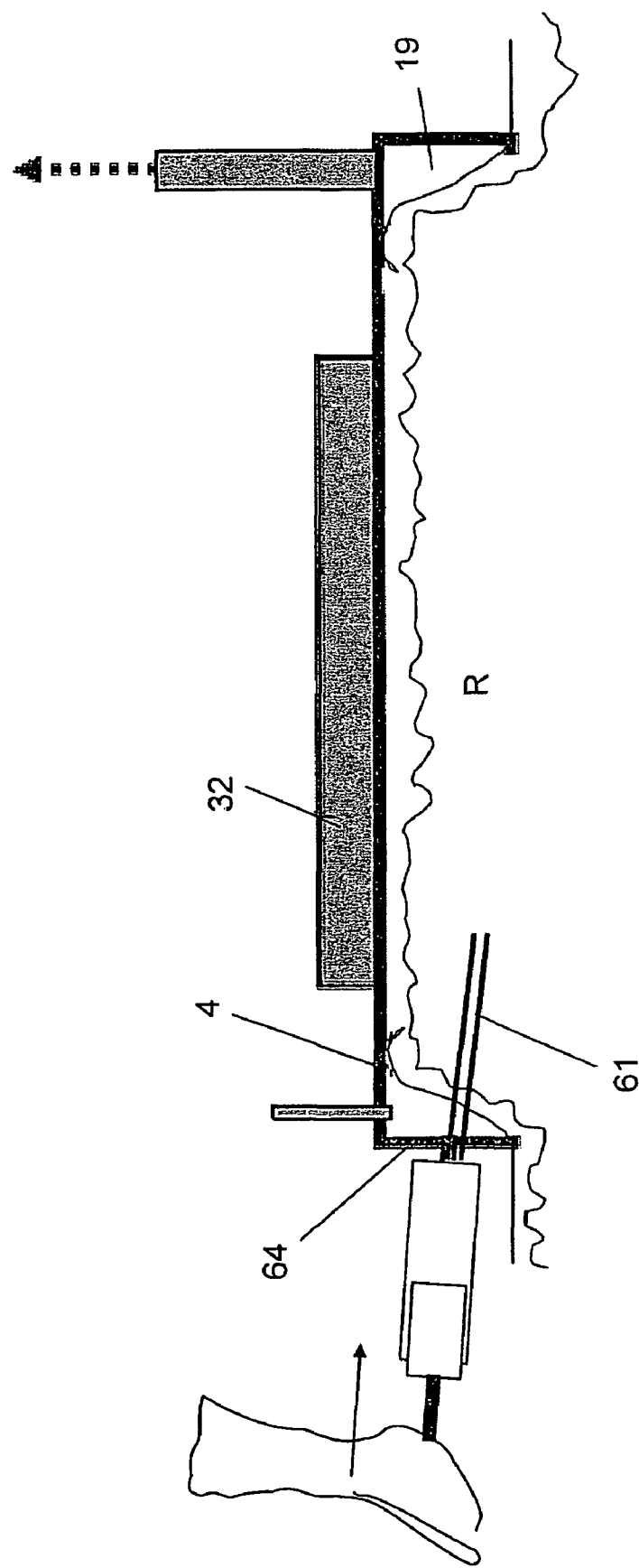
FIG. 9 schematically illustrates an injection method by which a needle pierces through the puncturable sidewalls of an evacuation chamber.

An elongated needle 61 may be injected into drawn skin region R through a cylindrical sidewall 64 of evacuation chamber 19, as shown in FIG. 9. When injection needle 61 penetrates through sidewall 64, an inwardly directed pressure-derived force acts on sidewall 64, compressing cover element 4 and interface element 32. In this injection method, interface element does not have to be subjected to any factory-produced compressive forces due to the pressure-derived self compression. A painless injection through a sidewall is advantageous for medical treatments such as the injection of collagen within the epidermis, essentially parallel to the skin surface, for wrinkle removal, a procedure which is normally very painful.

Figure 21:
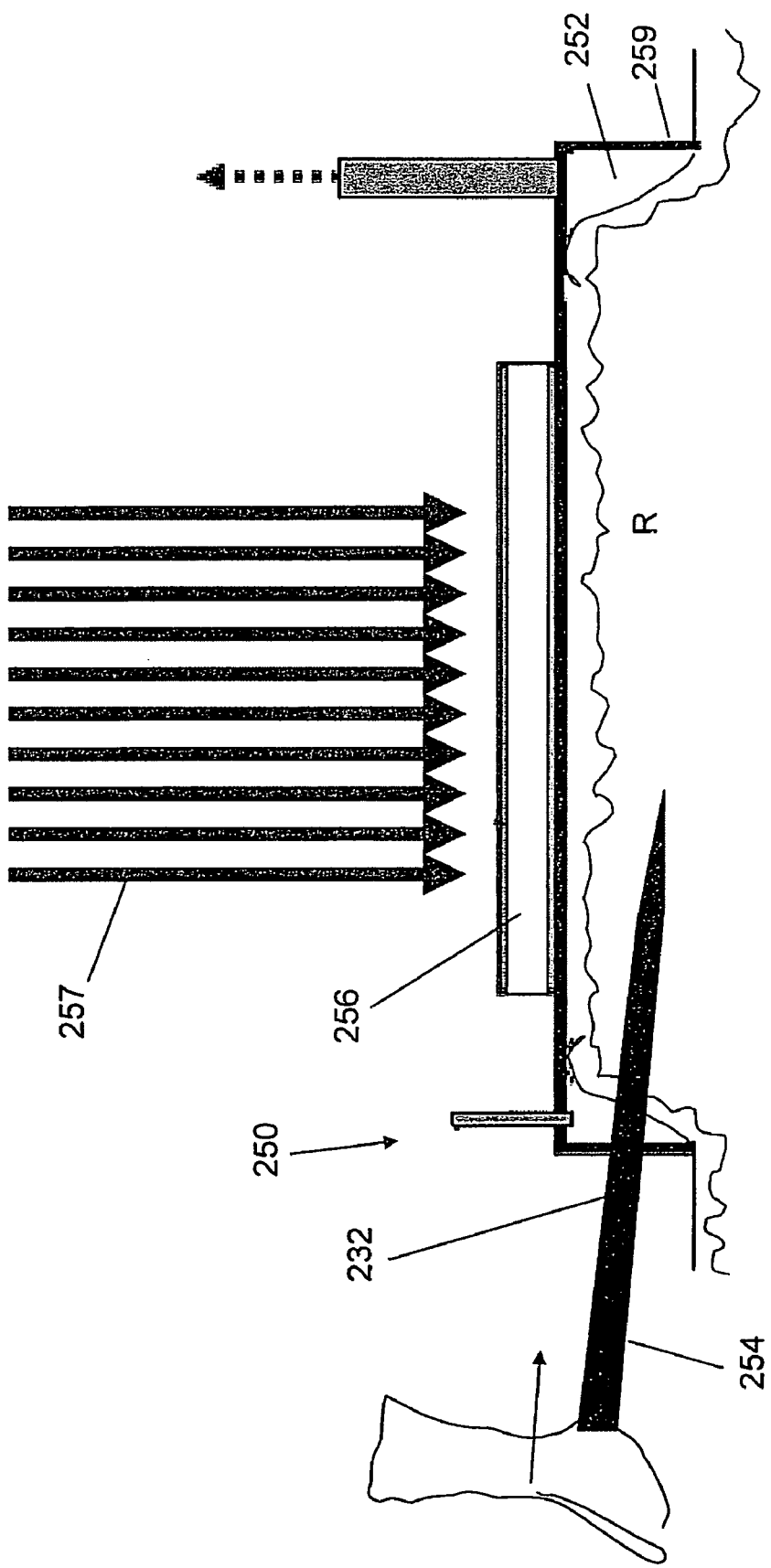
FIG. 21 schematically illustrates an apparatus for painlessly administering a dual light and needle based medical treatment.

In the embodiment of FIG. 21, apparatus 250 employs an evacuation chamber 252 by which a dual light and needle based medical treatment is painlessly administered. A dark, e.g. black, elongated needle 254 is inserted within the epidermis and substantially parallel to the skin surface in an identical way as injectors for collagen filling or for wrinkle reduction are introduced. However, needle 254 does not serve as an injector but rather as a thin blackbody, capable of attracting the optical energy of a laser or IPL beam 257 directed under the skin surface and consequently thermally damaging its surroundings. One suitable application for this apparatus is the contraction of wrinkles present in the vicinity of, and overlying, needle 254.

In order to inhibit the pain which is normally sensed during these types of treatment, a vacuum is generated within evacuation chamber 252. Evacuation chamber 252 comprises transmitting element 256 which is transparent to beam 257, to allow the latter to subcutaneously propagate to skin region R and heat needle 254, and puncturable sidewalls 259 so that needle 254 may penetrate the interface element and the adjoining skin region R. Needle 254, which may be produced from medical stainless steel galvanized in a black color having a diameter ranging from 50-1000 microns and a length of approximately 30 mm, is painlessly introduced through sidewall 259 to skin region R after a vacuum, e.g. of greater than 400 millibars, has been applied to evacuation chamber 252 and skin region R has been compressed by the underside of transmitting element 256 greater is size than the pain inhibiting threshold, e.g. 12×40 mm. Following introduction of needle 254 into skin region R, light beam 257 having an energy density ranging from 10-100 J/cm$^2$ is fired and the resulting photothermolysis effect is painless. A suitable laser for generating beam 257 is an Nd:YAG laser which produces a pulse duration of 10-300 millisec. The generated light is well absorbed in artificially blackened needle 254 and creates minimal damage to the skin. The blood expulsion caused by the compression of skin region R ensures that the heat conducted from the heated needle is transferred to the adjacent collagen fibers rather than to blood.

When the medical treatment is administered solely by means of a laser, the evacuation chamber may be provided with skin gliding apparatus. Very fast and painless treatments may be performed by gliding the laser unit distal end at a speed ranging from 0.3-40 cm/sec over an interface element made of sapphire through which the laser light can be transmitted. A gliding action is made possible by means of a suitable track formed in, or attached to, the interface element. The track supports the laser unit distal end, and is adapted to minimize friction between the laser distal end and the interface element, and to prevent the latter from being scratched. The skin gliding apparatus is preferably configured in such a way so as to maintain the laser unit distal end in a disposition which is substantially perpendicular with respect to the interface element and to prevent overlaps or voids between adjacent spots that are treated by the treatment light. Pain is absent due to the relatively large size of the interface element, which ensures that a sufficiently large number of pressure receptors are squeezed so that a signal transmitted therefrom inhibits reception of a pain signal, and due to the relatively high vacuum level. In contrast to prior art treatments wherein immediate sharp pain is felt during each treatment pulse, necessitating a patient to rest during a long delay before continuing the treatment or to be applied with a risky analgesic topical cream, the treatment speed of apparatus of the present invention employing an evacuation chamber need not be slowed.

For example, an evacuation chamber having a size of e.g. 20×40 mm is suitable for inhibiting pain in conjunction with treatment light generated by the Light Sheer diode laser having an energy density of 40 J/cm$^2$. The laser unit distal end may be displaced over a sapphire interface element at a speed of 10 mm every 0.5 seconds. The applied vacuum is maintained for a duration of 4 seconds, thereby allowing a skin surface having a similar area of 20×40 mm to be treated by the treatment light without having to release the vacuum.

Figure 22:
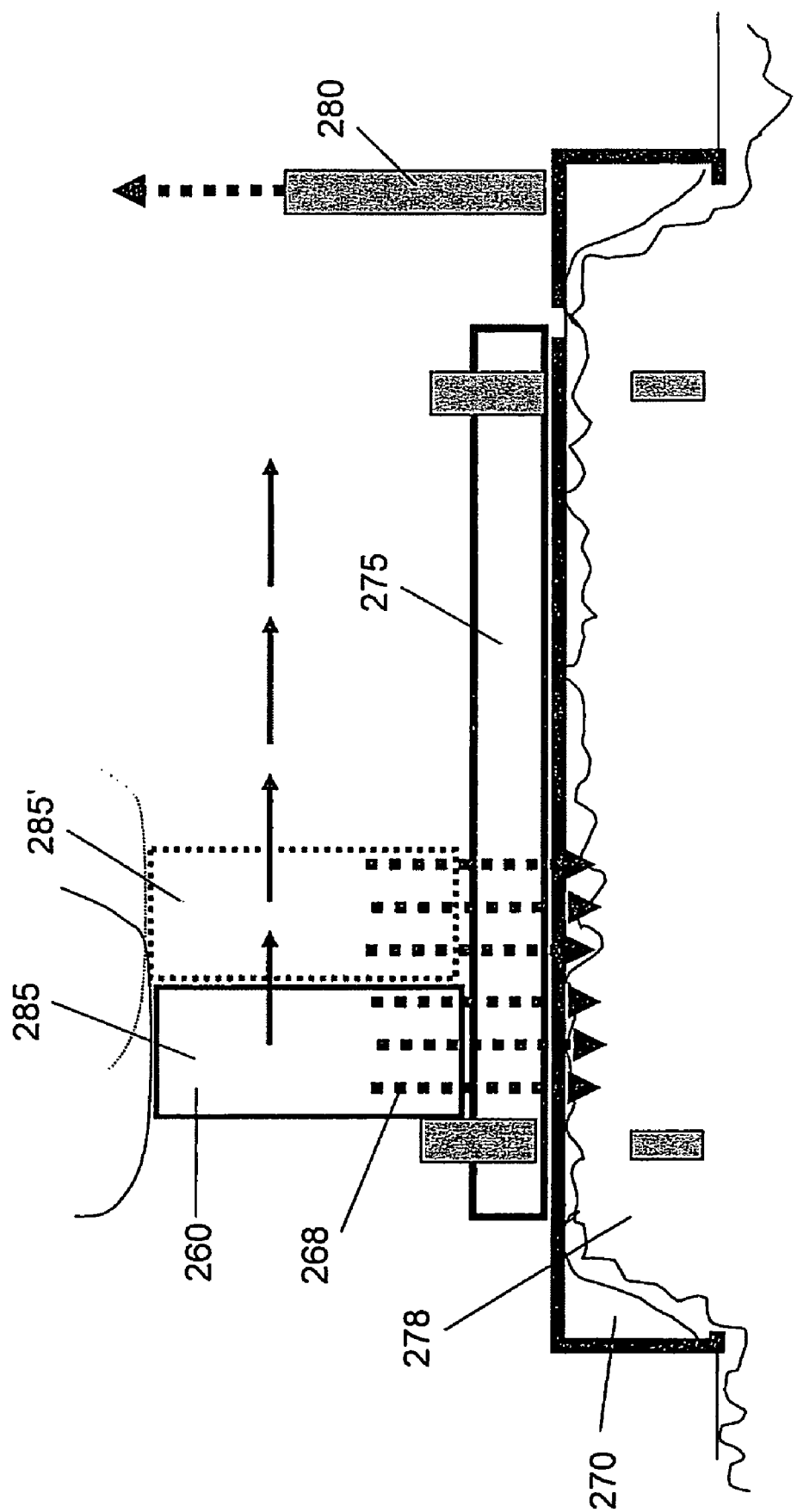
FIG. 22 schematically illustrates gliding apparatus used to displace a laser or IPL distal end along a large sized interface element of a pain inhibiting evacuation chamber.

FIG. 22 schematically illustrates the gliding of a laser distal end on the interface element of a vacuum chamber with respect to the following steps:

A) Laser distal end 260 is initially positioned in contact with the top of interface element 275 of evacuation chamber 270 at position 285.

B) Air is evacuated from vacuum chamber 270 via conduit 280 within 0.5 sec at a vacuum level of at least 500 mmHg which is suitable for inducing pain inhibition.

C) Treatment laser pulse 268 is fired at position 285 towards skin target 278 therebelow.

D) Laser distal end 260 is displaced to position 285' at a speed of L/t, where L is the beam diameter and t is the interval between laser pulses. The laser distal end may be automatically and cyclically repositioned if the gliding track is provided with equally spaced stations, whereat the laser distal end is urged to be stationary when light is emitted therefrom.

E) Treatment laser pulse 268 is fired at position 285' towards the skin target therebelow.

F) Steps D) and E) are repeated until laser distal end 260 is displaced along the entire surface area of interface element 275.

G) Laser distal end 260 is displaced to original position 285.

H) The vacuum within vacuum chamber 270 is released within 0.5 second.

I) Vacuum chamber 270 is raised and repositioned.

The displacement of laser distal end 260 may be externally triggered, i.e. by means of an optical detector that senses the presence of a marker on interface element 275 that corresponds to each target position. Alternatively, laser distal end 260 is driven by a suitable mechanism at a constant speed of L/t over interface element 275 in free running fashion, i.e. not externally triggered. For example, a laser distal end that produces a 12-mm diameter light beam, such as the Light Sheer of Lumenis, will be driven at a speed of 20 mm/sec if the laser is operated in a free running mode at a 2 Hz repetition rate. In the free running mode, a photodiode may be employed, which is adapted to detect a light pulse generated by the laser and to generate an audible signal being indicative that the laser distal end may be repositioned.

In another embodiment, gliding laser distal end 260 is fired in response to a texture sensing mechanism. A texture sensing mechanism is operable in conjunction with a laser such as the Fraxel® laser produced by Reliant Technologies Inc., USA, which is suitable for skin rejuvenation and known to be very painful. The Fraxel® laser is generally activated upon detecting the presence of a blue dye which is applied to the skin and helps to identify a skin target desired to be treated by laser beam 268. In this embodiment of the present invention, a texture associated with interface element 275, such as a blue dye or a poorly polished portion of the interface element, may activate the Fraxel-type laser when the presence of the texture is sensed. When a vacuum is applied to evacuation chamber 270 and skin target 278 is compressed and flattened against interface element 275, the skin target is disposed in relatively close proximity to distal end 285 of the laser. The laser may function in similar fashion as the Fraxel® laser; however, if a sufficiently high vacuum level is applied to evacuation chamber 270, the selected medical treatment will be painless.

Figure 13:
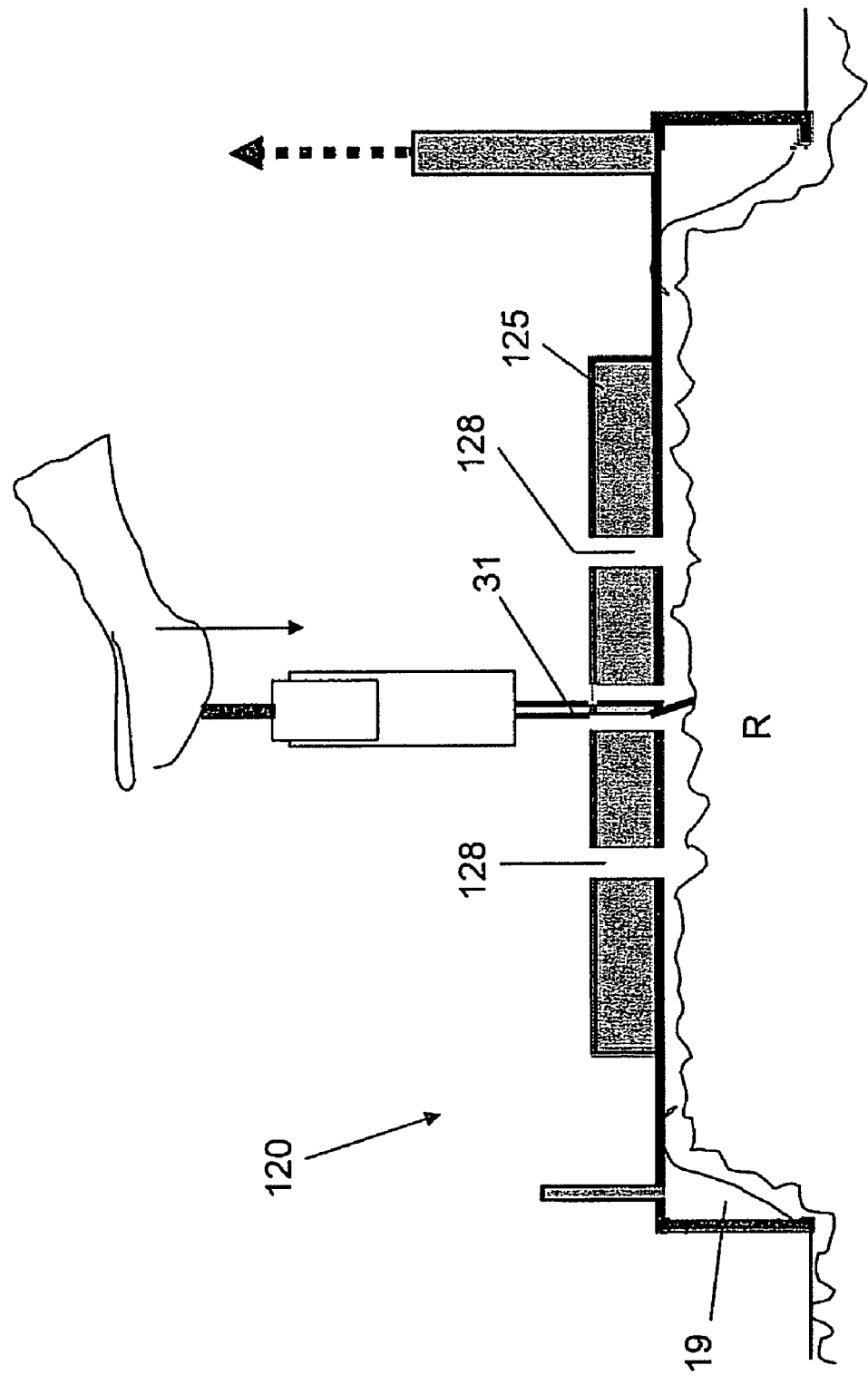
FIG. 13 schematically illustrates an evacuation chamber having an apertured interface element.

Apertured interface element 125 shown in FIG. 13 is also useful when the medical treatment is administered solely by means of a laser. A normally painful sensation will be inhibited if the vacuum level applied to evacuation chamber 19 is sufficiently high, e.g. 400 mmHg and the surface area of interface element 125 is sufficiently high, e.g. 15×25 mm. Apertures 128 are advantageous in that the generated laser beam can propagate therethrough in order to impinge on skin region R when not able to be transmitted through the material from which interface element 125 is composed. When Ruby Q-switched, frequency doubled Nd:YAG, Nd:YAG, or Alexandrite lasers having an energy density ranging from 4-12 $J/cm^2$ and a pulse duration ranging from 1-20 nanosec are employed, for example, for the removal of tattoos or the treatment of pigmented lesions, the transmitting interface element is liable to shatter or a coating applied to the interface element is liable to decompose. However, when the laser beam is directed through an aperture 128 having a diameter of approximately 4 mm, the optical energy of the laser beam will not be absorbed within the interface element. Other lasers that may be operated in conjunction with an apertured interface element is an ablative laser such as a $CO_2$ or Erbium laser.

Figure 18:
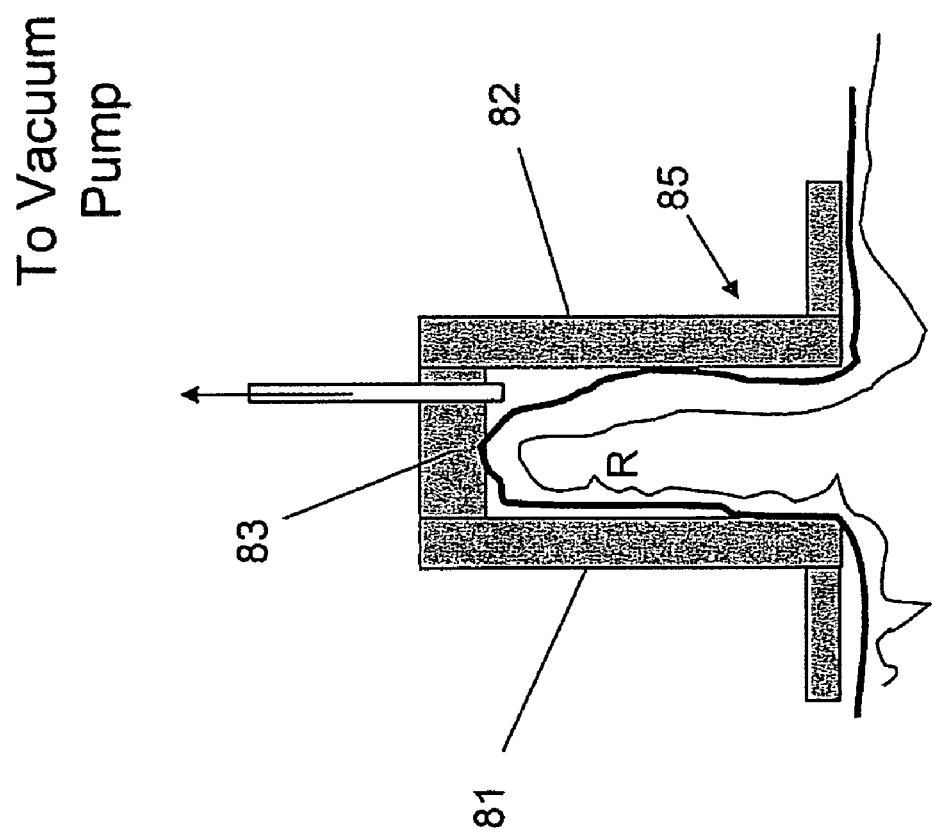
FIG. 18 schematically illustrates an evacuation chamber configured as a slit.

In another embodiment of the invention illustrated in FIG. 18, evacuation chamber 85 is configured as a slit defined by elongated, planar sidewalls 81 and 82 and by a rigid upper surface 83 extending between, and having a considerably shorter length than, sidewalls 81 and 82. For example, upper surface 83 may have a surface area of 10×50 mm and skin region R can be drawn to a height of 10 mm. After the vacuum pump is activated, skin region R is drawn through the interior of slit 85 and is compressed against surfaces 81-83. The compressing effect of skin region R is similar to a certain extent to that of skin pinching, although, as described hereinabove, the physiological reaction to vacuum generated compression is much different than the application of a positive pressure onto a skin surface. The injection needle is introduced through one of the sidewalls 81 or 82, which are puncturable.

Figure 19:
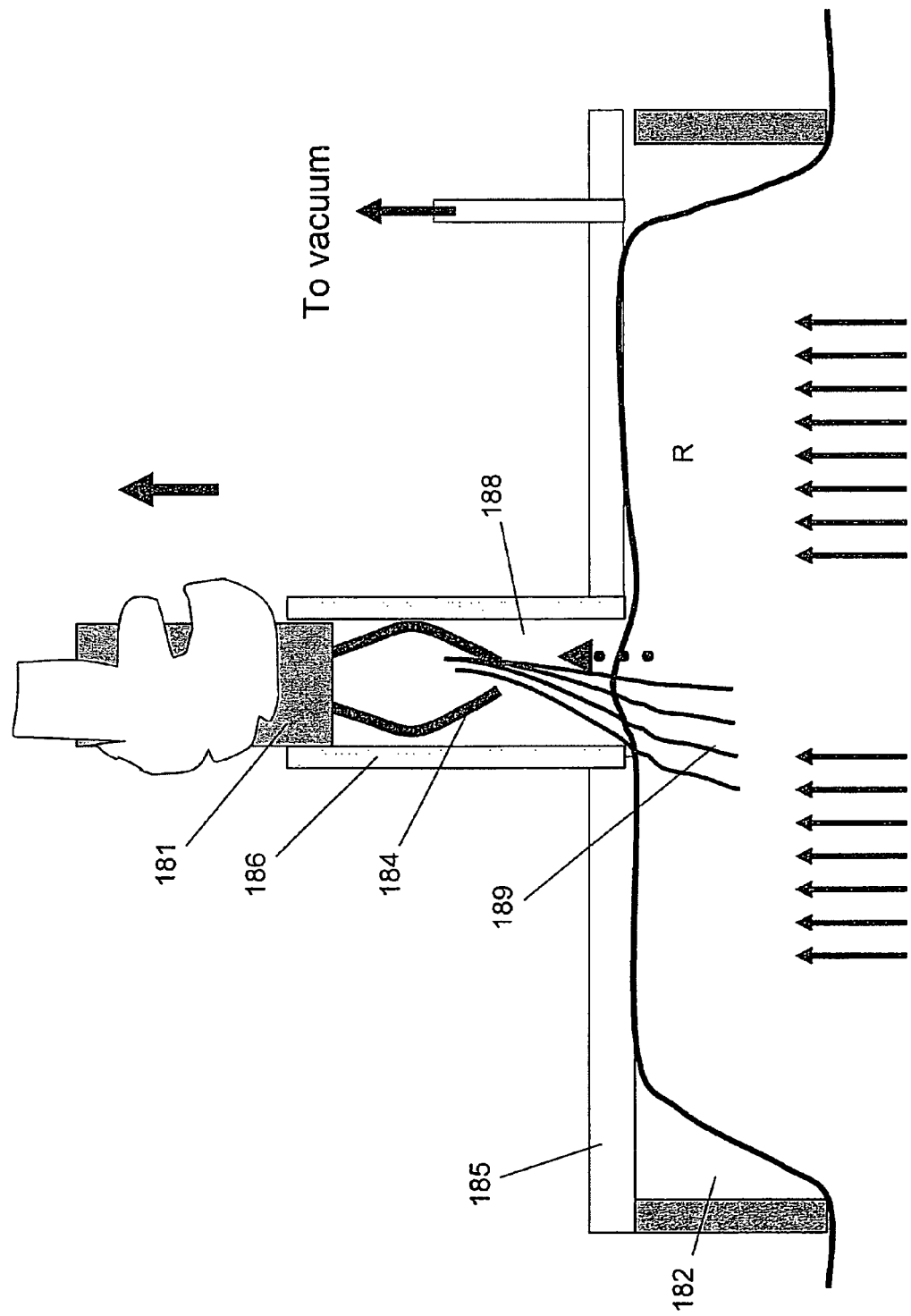
FIG. 19 schematically illustrates a painless tweezers-based hair removal procedure carried out in conjunction with the evacuation chamber of the present invention.

In the embodiment of FIG. 19, painless hair removal is carried out by removing a bundle of hair shafts with the use of tweezers. To enable the introduction of tweezers 184 into evacuation chamber 12, outer and inner interface elements are employed. Outer interface element 185 is planar and horizontally extending and is formed with a central aperture (not shown), in which inner interface element 186 is inserted, such as with a press fit. Inner interface element 186 is a vertically extending cylinder, and its inner diameter is substantially equal to the outer diameter of piston 181 to which is connected tweezers 184. When the vacuum is being applied, inner interface element 186 is covered and skin region R is compressed against the bottom surface of outer interface element 185 and inner interface element 186. The inner interface element cover (not shown) is then removed and piston 181 is introduced into interior 188 of inner interface element 186 as shown so that tweezers 184 will be able to grasp and pull hair shafts 189 through the inner interface element interior 188. Since piston 181 substantially occludes interior 188, the vacuum level within evacuation chamber 182 is not significantly reduced and hair shafts 189 may therefore be painlessly removed. This hair removal procedure is very painful when a vacuum is not generated within evacuation chamber 182 and skin region R is not compressed against outer interface element 185.

Figure 10B:
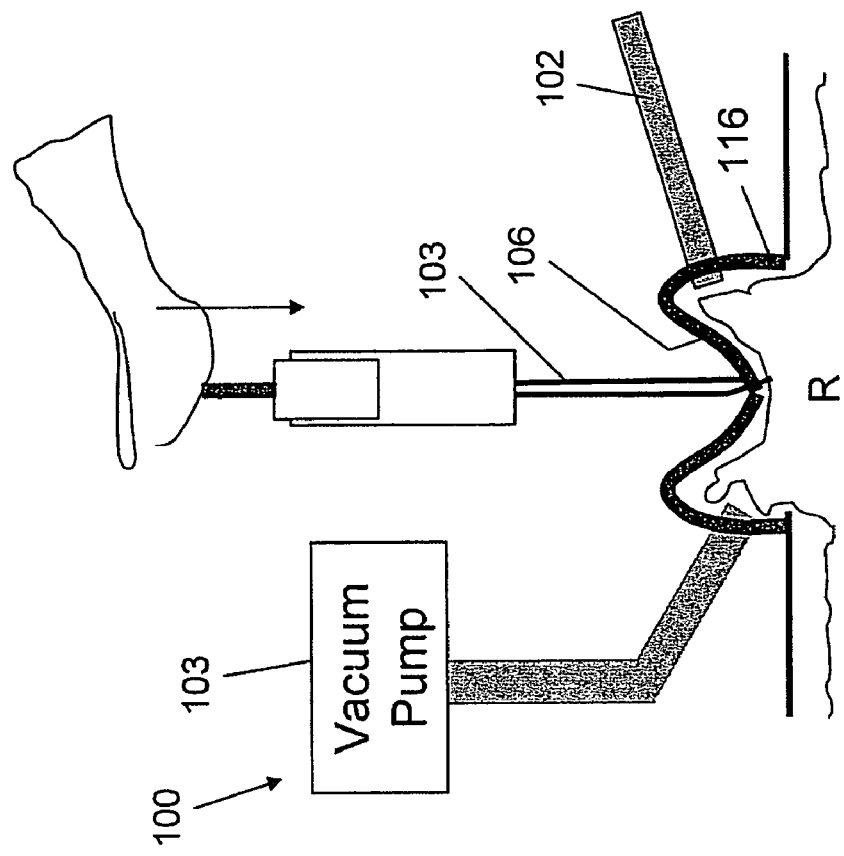
FIGS. 10*a-b* schematically illustrate a convex and concave interface element, respectively.
Figure 10A:
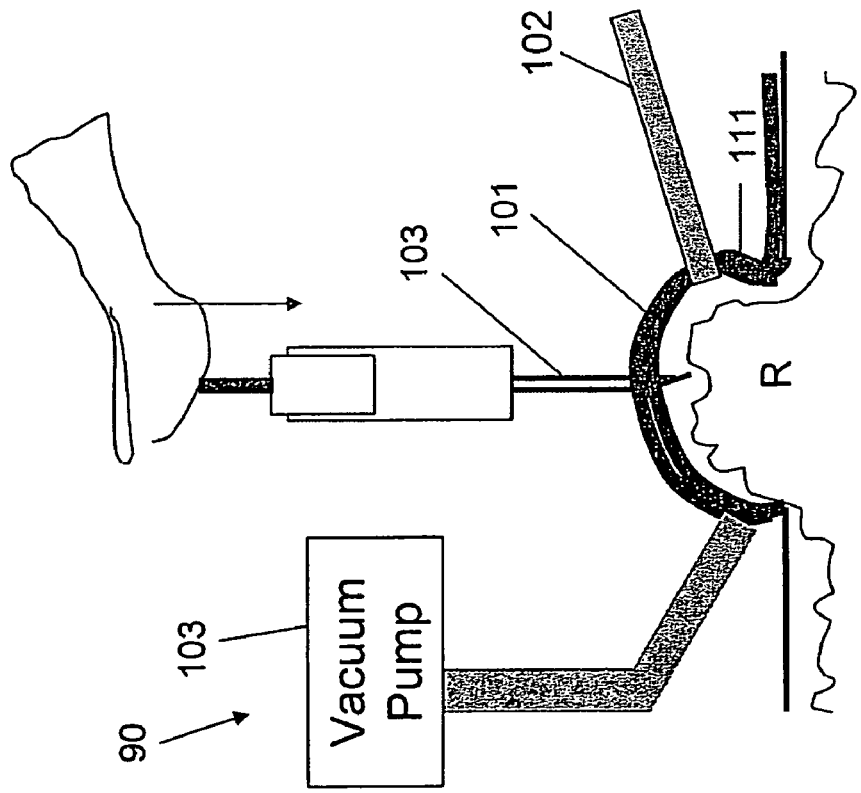
Figure 12:
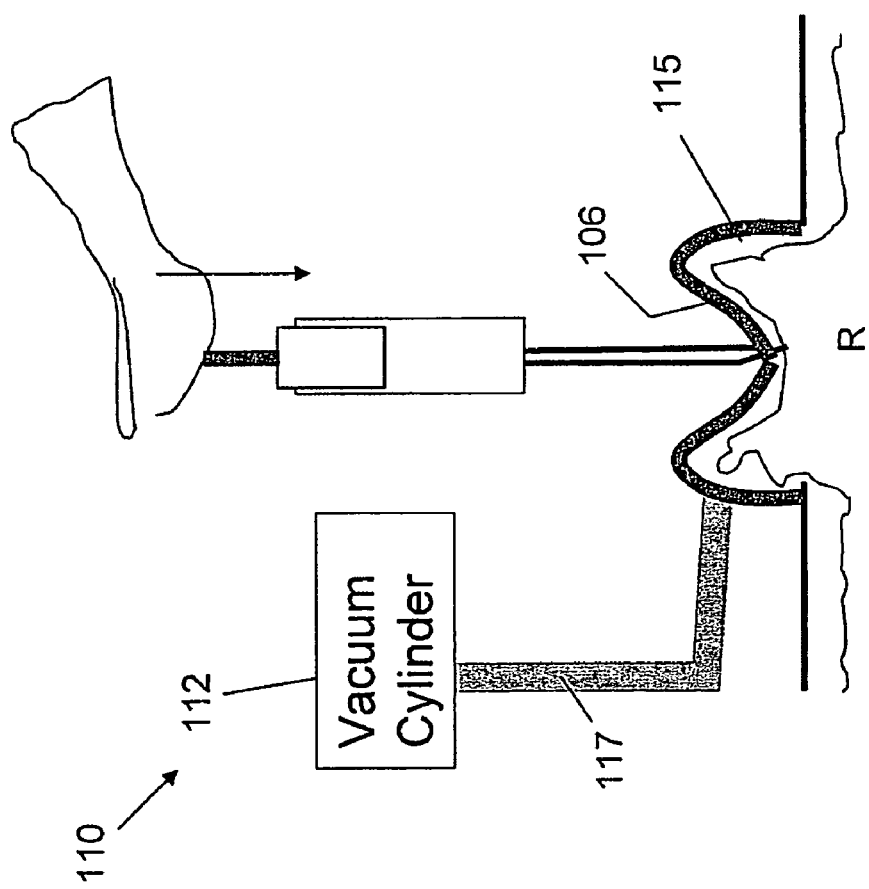
FIG. 12 schematically illustrates an evacuation chamber having a concave interface element in which a vacuum is generated by means of a pre-evacuated vacuum source.

In another embodiment of the invention illustrated in FIGS. 10*a*-*b* and 12, the interface element is curvilinear, whether a convex interface element 101 shown in FIG. 10*a* or a concave interface element 106 shown in FIGS. 10*b* and 12. Convex interface element 101 shown in FIG. 10*a* is retained by a short, substantially vertical sidewall 111. Concave interface element 106 shown in FIG. 10*b* is retained by inwardly curved sidewall 116. A curvilinear interface element configuration is advantageous in that air introduced into the evacuation chamber via the puncture, which is caused by the injection of needle 103 into skin region R, due to the pressure differential between the air side and vacuum side of the evacuation chamber, will be vertically directed. Consequently the degree of compression of skin region R against the rigid interface element and the resistance to tearing of the interface element will be increased.

Apparatus 90 and 100 shown in FIGS. 10*a* and 10*b*, respectively, comprise vacuum pump 103 and a control unit (not shown) for generating the vacuum within the corresponding evacuation chamber prior to the injection and releasing the vacuum following the injection, in accordance with a selected sequence and in response to the vacuum level detected by pressure sensor 102.

Apparatus 110 shown in FIG. 12 comprises a pre-evacuated vacuum cylinder 112 for generating the vacuum within evacuation chamber 115 and means (not shown) such as a valve for isolating vacuum cylinder 112 from evacuation chamber 115. Evacuation chamber 115 may be disposable, and the means for isolating vacuum cylinder 112 therefrom may therefore be a breakable stop. Pressure sensor 102 (FIG. 10*b*) may also be employed to achieve a suitable pain alleviating vacuum level within evacuation chamber 115.

When skin contact sensor 221 (FIG. 2) is employed to detect the placement of evacuation chamber 115 on skin region R, the means for isolating vacuum cylinder 112 from evacuation chamber 115 may be automatically opened. Once skin contact sensor 221 detects the placement of evacuation chamber 115 on skin region R, the isolation means is automatically opened and a vacuum is applied to evacuation chamber 115 via conduit 117 in communication with vacuum cylinder 112. Since the opening of the isolation means, which is an operation generally not suitable for those of limited dexterity, may be automatically performed, and since evacuation chamber 115 need not be sanitized when a disposable evacuation chamber is employed, an injection may be painlessly self-administered. Since a vacuum pump is not needed, the apparatus is affordable, and therefore such an arrangement is particularly suitable for an insulin injection device which is used on a daily basis.

Apparatus 120 schematically illustrated in FIG. 13 comprises planar interface element 125 formed with a plurality of apertures 128 through each of which flattened skin region R may be injected. The use of an apertured interface element is advantageous in that, while substantially all of skin region R is flattened, the skin surface underlying each corresponding aperture 128 may be injected without contacting the bottom surface of interface element 125, so as to avoid a lack of biocompatibility to the material of interface element 125 or a lack of sterilization.

Apertures 128 need to be sufficiently small to ensure that the downwardly directed force, which is caused by air flow through the apertures as a result of the pressure differential of the air external and internal to the evacuation chamber, will be considerably smaller than the upwardly directed vacuum-generated force which urges skin region R to be in compressed relation with the bottom surface of interface element 125, in order to maintain the vacuum level within evacuation chamber 19. In order to ensure sufficient afferent inhibition, the applicant has found that the total surface area of the apertures should not be greater than 20% of the enclosed surface area of a planar interface element. When the interface element is curvilinear, as shown in FIGS. 10a-b, the upwardly directed vacuum-generated force will be increased and the infiltration of ambient air through the apertures will be proportionally decreased.

Figure 17:
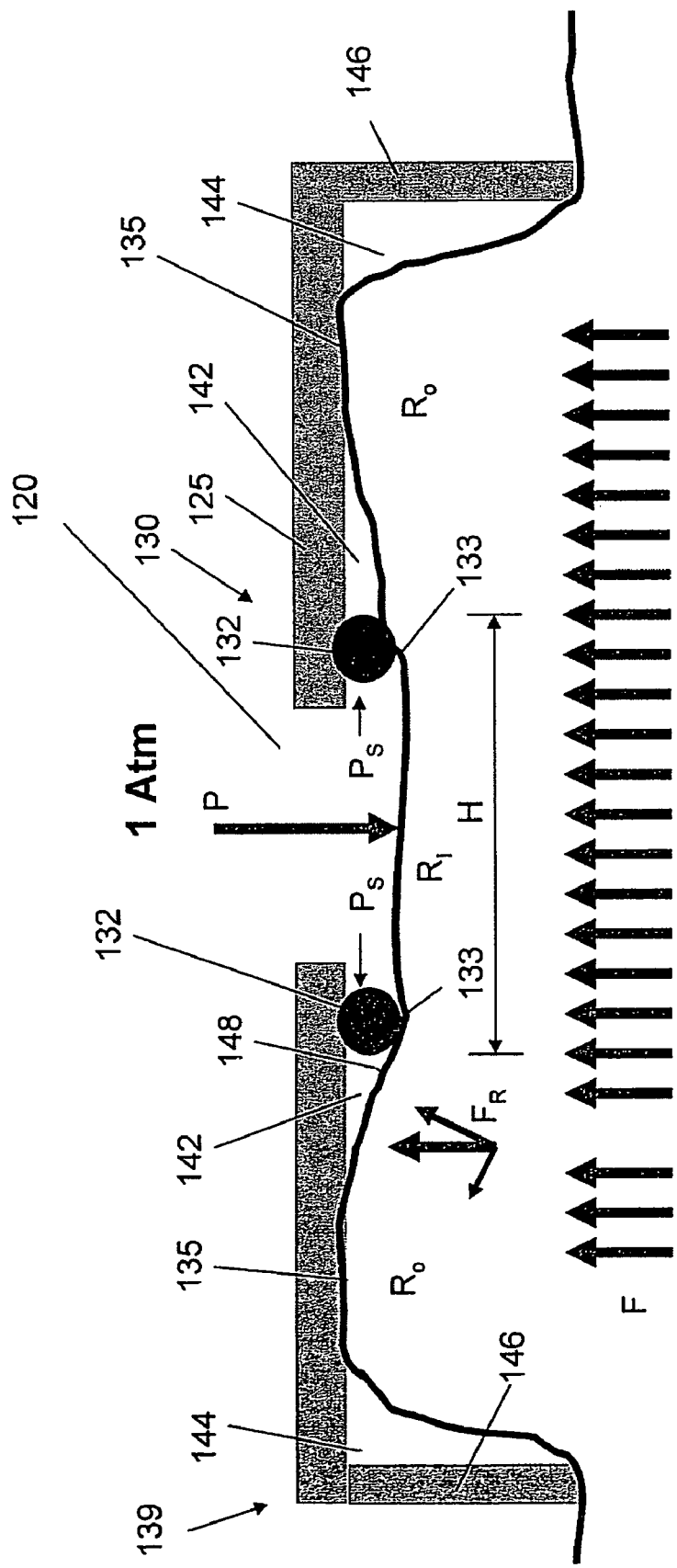
FIG. 17 schematically illustrates means for maintaining the vacuum within an evacuation chamber following deactivation of the vacuum pump.

In the embodiment of FIG. 17, apparatus 130 is adapted to maintain the vacuum within evacuation chamber 139 and the resulting skin compression after the operation of the vacuum pump, or any other suitable vacuum generating means, has been terminated. Apparatus 130 comprises rim 132 of diameter H, which is connected to the underside of apertured interface element 125 and encircles aperture 120 through which a needle is introduced prior to injection into the skin region. Rim 132 may be an O-ring or may be integrally formed together with interface element 125.

As a vacuum is applied to evacuation chamber 139, an upward directed vacuum-derived compression force F is generated within the skin region, drawing the latter in compressed fashion towards apertured interface element 125. For sake of clarity, the skin region is shown to be subdivided into inner portion $R_I$ underlying aperture 120 and outer portion $R_O$ surrounding inner portion $R_I$. Due to the presence of rim 132, terminal surface 133 of inner portion $R_I$ bordering with outer portion $R_O$ abuts rim 132 and inner portion $R_I$ is therefore prevented from contacting interface element 125. However, large-area interface engaging surface 135 of outer portion $R_O$ is allowed to contact interface element 125, and therefore the entire skin surface of outer portion $R_O$ is disposed above the entire skin surface of inner portion $R_I$. The skin surface of inner portion $R_I$ remains in a substantially horizontal disposition due to the influence of the downward directed atmospheric pressure derived force P. Although inner portion $R_I$ which is not compressed by interface element 125 is punctured by the injection needle, the pain sensation is inhibited by the afferent inhibition generated by the compression of outer portion $R_O$ surrounding inner portion $R_I$ onto interface element 125.

When a vacuum is applied to evacuation chamber 139 and interface engaging surface 135 of outer portion $R_O$ is compressed against interface element 125, two volumes of negative pressure are produced within evacuation chamber 139: volume 142 enclosed by interface element 125, rim 132, and outer skin portion $R_O$, and volume 144 enclosed by interface element 125, sidewall 146 of evacuation chamber 139, and outer skin portion $R_O$. Even though rim 132 is subjected to a radial force $P_S$ generated by the pressure differential between atmospheric pressure and the vacuum level within volume 142, rim 132 is not severed from interface element 125. The reactive force $F_R$, which is normal to skin surface 148 extending between rim 132 and interface engaging surface 135, applies a force onto rim 132 which counteracts radial force $P_S$, thereby ensuring the continued presence of volume 142.

Even after the termination of the vacuum generating means which induced the compression of interface engaging skin surface 135, a vacuum advantageously remains in volumes 142 and 144. Due to the presence of volumes 142 and 144, an upwardly directed vacuum-derived compression force F remains, although its magnitude is considerably less than when the vacuum generating means was operable, and inter-face engaging skin surface 135 continues to be compressed by interface element 125, although the area of interface engaging skin surface 135 is reduced as a result of the lower magnitude of compression force F. A vacuum remains in volumes 142 and 144 as long as the magnitude of upwardly directed compression force F is sufficiently great so as to ensure that outer skin portion $R_O$ contacts both interface element 125 and rim 132. A significant parameter in determining the ability of apparatus 130 to maintain the vacuum within evacuation chamber 139 after the operation of the vacuum generating means has been terminated is diameter H of rim 132. If diameter H of rim 132 is excessively small, outer skin portion $R_O$ will contact interface element 125 and rim 132 for a shorter period of time. For example, the inventors have determined that a rim diameter of 0.7 mm is able to maintain a vacuum level of 0.5 atm for a duration of over 1 minute.

Figure 14A:
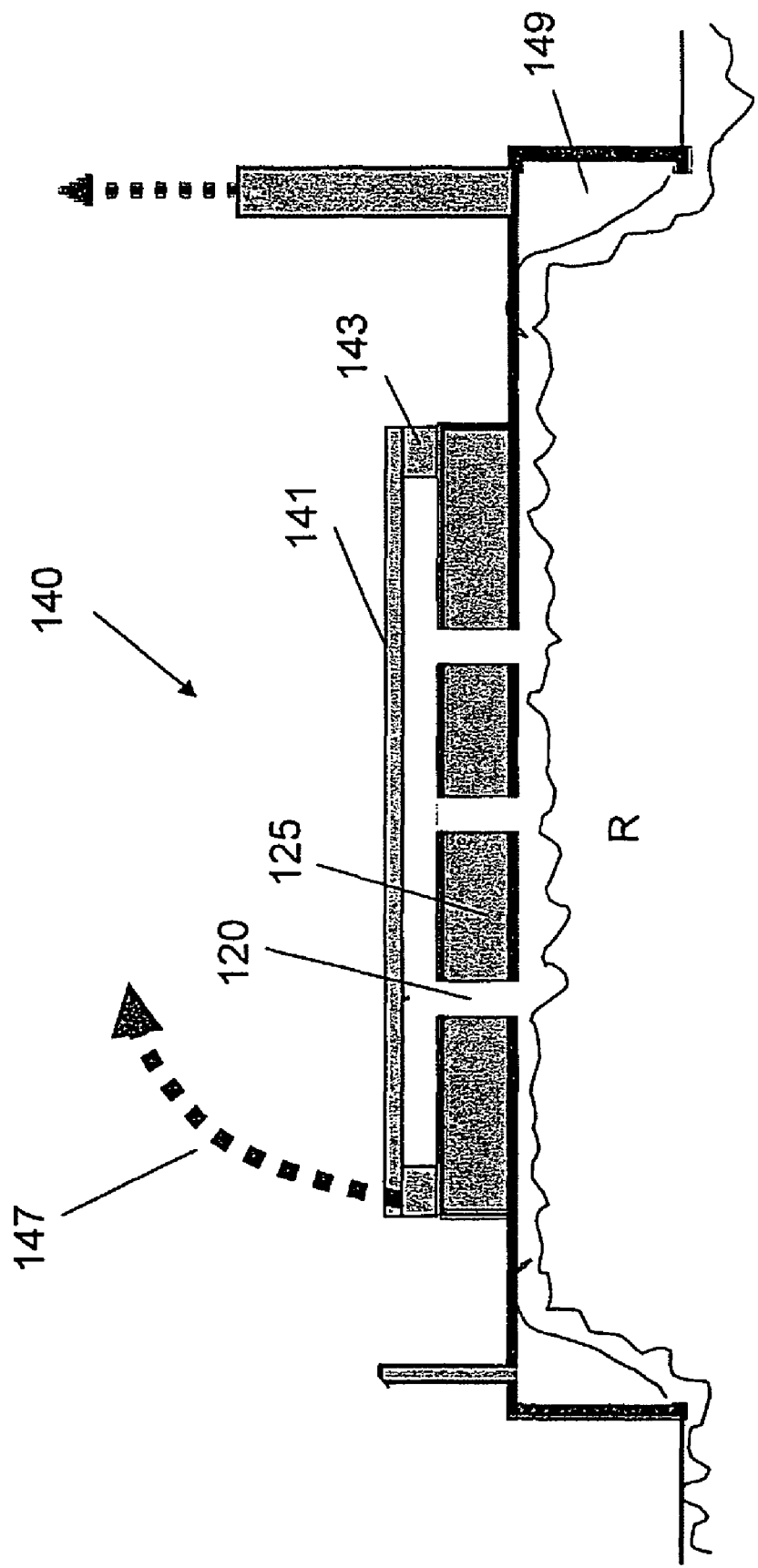

In the embodiment of FIGS. 14a-b, apparatus 140 is adapted to minimize the infiltration of ambient air through apertures 120 of interface element 125 by employing shield element 141. Shield element 141 shown in FIG. 14a may be placed directly on top of interface element 125, or alternatively seal element 143 may be interposed between shield element and interface element 125. By covering interface element 125 with shield element 141 prior to applying the vacuum, infiltration of ambient air through apertures 120 is minimized and the vacuum level within evacuation chamber 149 can be consequently increased. Shield element 141 may be a thin sheet of polymer, such as cellophane, mylar, Kapton®, and nylon, or may be cloth suitable for sterile packing and bandages, and its thickness may range from 10-50 microns. After the vacuum is applied and skin region R is drawn and compressed against interface element 125, shield element 141 is removed or peeled as represented by arrow 147 in preparation of a skin injection while the generated vacuum is maintained due to the small size of apertures 120. In FIG. 14b, needle 31 is shown to be injected into skin region R, after shield element 141 has been peeled and needle 31 has been introduced into a selected aperture 120.

Figure 20A:
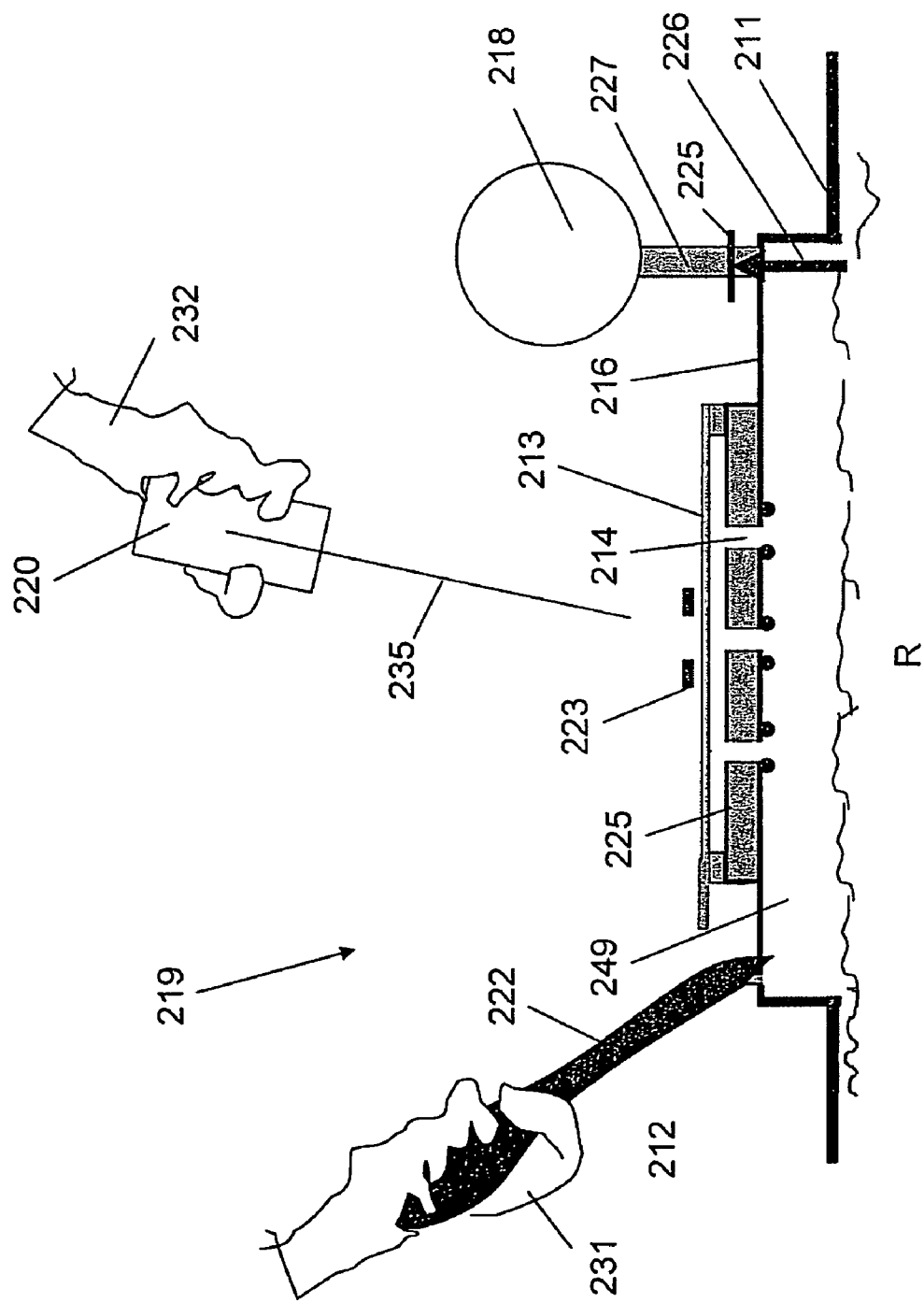
Figure 20B:
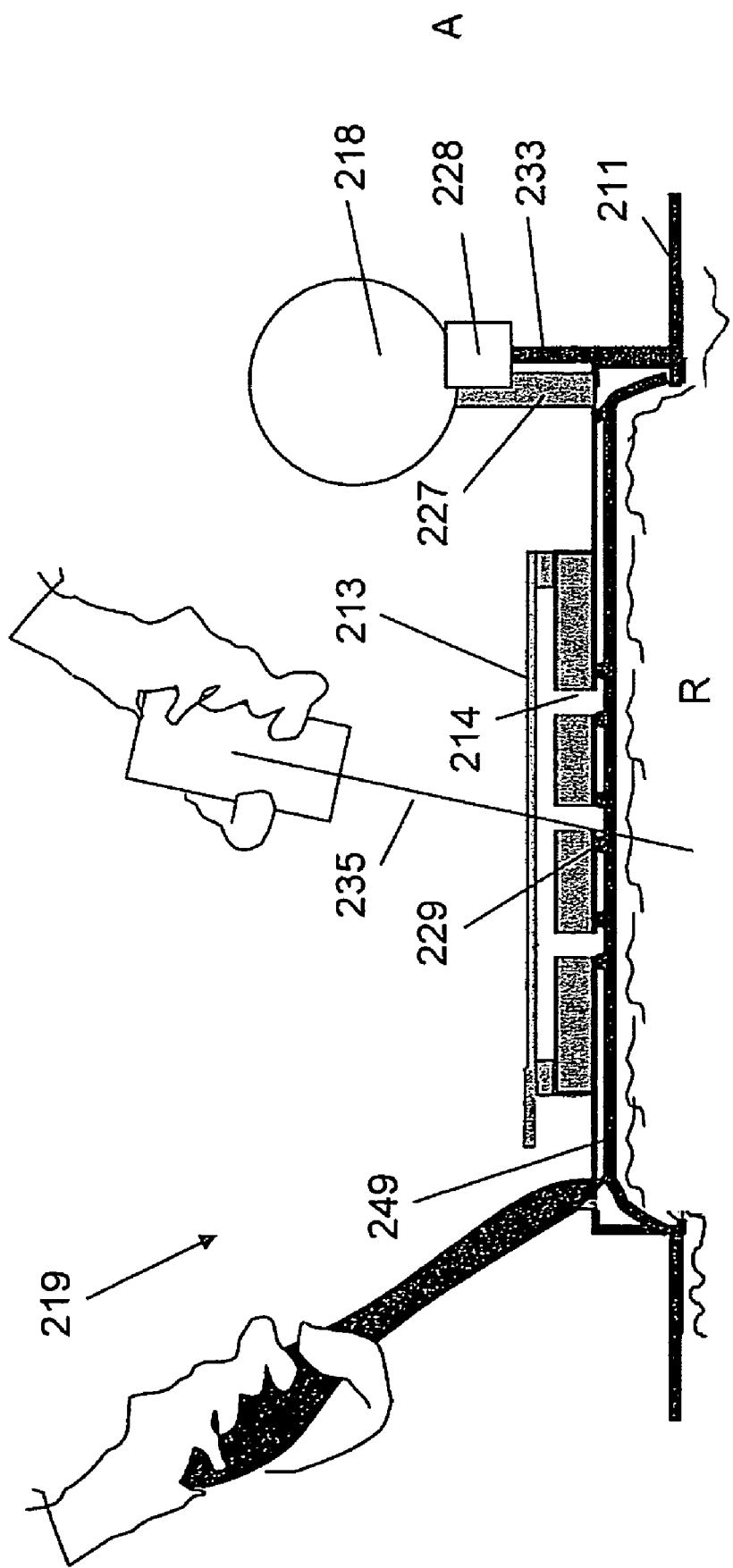

In the embodiment schematically illustrated in FIGS. 20a-b, which may be considered the preferred embodiment of the present invention, apparatus 219 enables a single health professional to position evacuation chamber 249 into which skin region R is drawn prior to the medical treatment, generate the vacuum therein, and administer the injection. FIG. 20a illustrates the positioning of evacuation chamber before the application of vacuum therein and FIG. 20b illustrates the administration of an injection after a skin region is drawn by the vacuum applied to the evacuation chamber.

Evacuation chamber 249 has a rigid planar cover element 216, the surface area of which is greater than the threshold pain inhibiting area. Cover element 216 may be made of polycarbonate or any other rigid polymer which can be sterilized in ethylene oxide or by means of radioactive irradiation. Apertured interface element 225 is retained within cover element 216 and is covered by thin, adhesive and puncturable shield element 213, e.g. the Tegaderm™ HP Transparent Dressing produced by 3M, USA. Marks 223 may be indicated on the upper face of shield element 213, to assist in directing injection needle 235 to apertures 214 formed in interface element 225. Rims 229, e.g. an O-ring, may be added to the underside of rigid cover element 216 in maintain the vacuum once the injection needle pierces shield element 213. Cover element 216 may be formed with an integral rim protruding from the underside thereof. To position evacuation chamber 149 above skin region R, handle 222 connected to cover element 216 of the evacuation chamber is held by a first operator hand 231.

Apparatus 219 employs vacuum source 218, which is embodied by a spherical container. Air is evacuated from vacuum source 218 to a relatively high vacuum level, e.g. 50 millibar, and conduit 227 connected to cover element 216 and extending from vacuum source 218 to evacuation chamber 249 is sealed. The volume of vacuum source 218 is sufficiently large to induce fluid flow thereto at a relatively high rate from evacuation chamber 249, when conduit 227 is in fluid communication with evacuation chamber 249, so that the generated vacuum level will be greater than the threshold pain inhibiting level. The volume of vacuum source 218 should be at least twice the volume of evacuation chamber 249. During tests conducted by the applicant, a high level of pain inhibition was sensed when vacuum source 218 was five times the volume of evacuation chamber 249.

In one embodiment, pins 226 located below vacuum source 218 are used to allow conduit 227 to be in fluid communication with evacuation chamber 249. After vacuum source 218 is evacuated and sealed by rubber membrane 225 stretched across the interior of conduit 227, the latter may be opened by perforating membrane 225. By placing a pin 226 on skin region R and below conduit 227, the pointed end of pin 226 perforates membrane 225 as evacuation chamber 249 is lowered and placed on skin region R. This configuration facilitates reuse of the apparatus. Following injection of beneficial material into one skin region and release of the vacuum, evacuation chamber 249 may be repositioned to another skin region. After a new membrane 225 is resiliently stretched and inserted within a suitable slit formed in conduit 227, the interior of vacuum source 218 may be evacuated through a valve in communication therewith (not shown) and by means of an external vacuum pump.

Once evacuation chamber 249 is lowered on skin region R and a vacuum is generated by means of vacuum source 218, skin region R is drawn and compressed against cover element 216 within a short period of time, e.g. less than 0.5 second. A fast and reliable vacuum generating capability is of great importance to patients and to health professionals operating the apparatus, to ensure pain inhibition. The vacuum level within evacuation chamber 249 and sterility of skin region R are increased by using thin sheet 211 surrounding evacuation chamber 249 and shield element 213 covering apertured interface element 225. Pain inhibition is made possible by employing an evacuation chamber 249 having a relatively large skin engaging area, e.g. the total area of cover element 216 and the bottom of interface element 225 is 20×40 mm, in order to gate pain nerves by transmitting pressure signals to the dorsal horn through the pressure nerves following compression of a sufficiently large enough number of pressure receptors, regardless of the pain level that would be generated by injector 220 if apparatus 219 were not employed.

Needle 235 is preferably injected in skin region R within approximately 2 seconds following generation of the vacuum within evacuation chamber 249 since the duration of pain inhibition is limited by a period of approximately 3 seconds following generation of the vacuum. While only a limited number of injector types may be used in conjunction with prior art vacuum-assisted injection devices, any commercially available injector may be employed in conjunction with the apparatus of the present invention. Nevertheless, the selected injector should be able to inject beneficial material into skin region R within 2 seconds, as explained hereinabove. Marks 223 assist the health professional administering the injection to properly position needle 235 over an aperture 214 prior to the injection.

Apparatus 219 is preferably provided with means for automatically releasing the vacuum from evacuation chamber 249, as shown in FIG. 20b. The vacuum release means is adapted to release the vacuum from evacuation chamber 249 at a predetermined interval following generation of the vacuum therein. Consequently, injection needle 235 may be retreated and evacuation chamber 249 may be repositioned to another skin region after injection. The vacuum may be released by means of mechanism 228 and a spring loaded plunger 233, e.g. connected to sheet 211. Plunger 233 is actuated upon placement of evacuation chamber 249 on skin region R and is caused to extend within mechanism 228. As plunger extends within mechanism 228, a valve (not shown) in communication with which both conduit 227 and the surrounding ambient air A is opened by means of a suitable gear train within a short period of time, e.g. 3-4 seconds. Alternatively, the vacuum release means may be embodied by electrically operating components, such as skin contact sensor 221 (FIG. 2) and a valve actuator of mechanism 228, which is in electrical communication with skin contact sensor 221.

Figure 15:
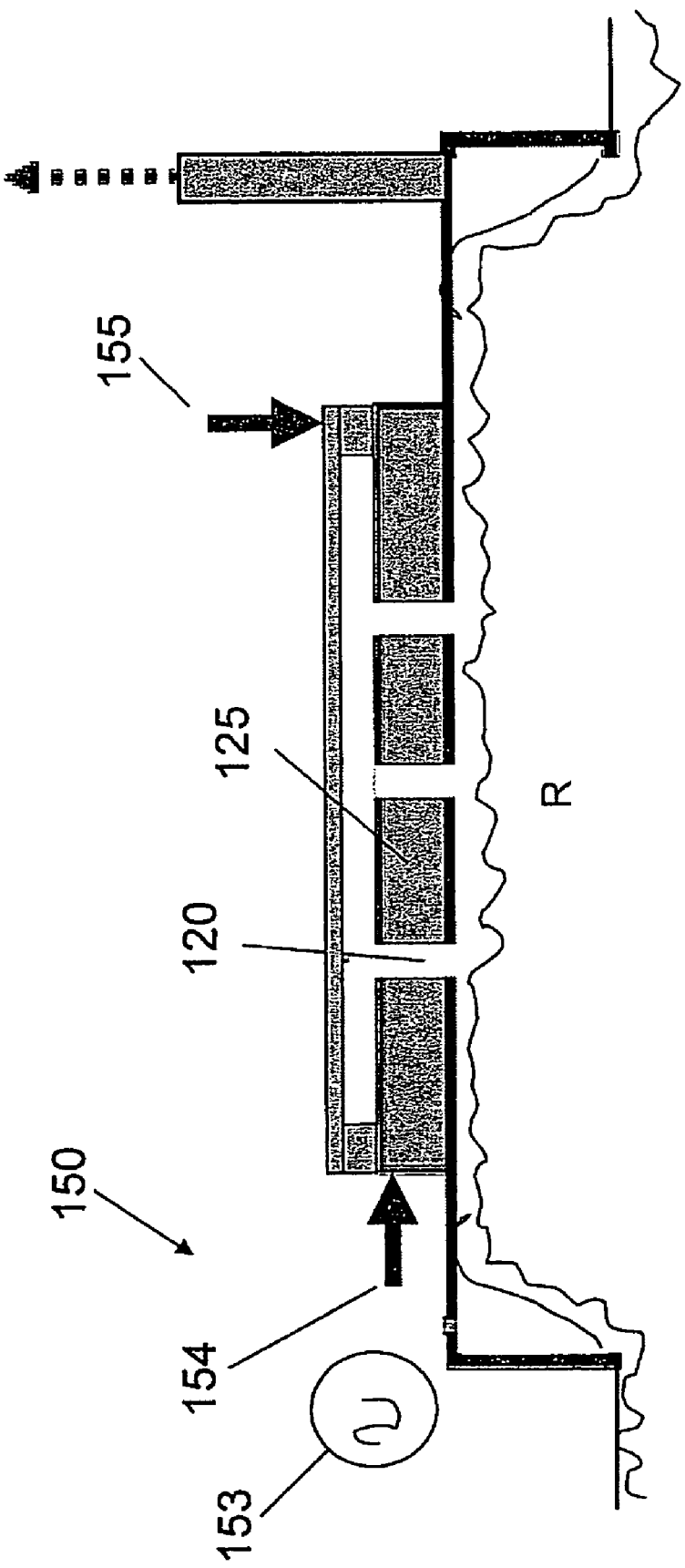
FIG. 15 schematically illustrates a vibrating interface element.

In the embodiment schematically illustrated in FIG. 15, apparatus 150 comprises a vibrator 153 driven by a miniature motor or by a small AC electromagnet, e.g. one manufactured by Vibraderm Inc, USA. Vibrator 153 is kinematically connected to apertured interface element 125 such that the generated vibrations may be horizontally directed as shown by arrow 154 or vertically directed as shown by arrow 155. Vibrator 153 may be operated both before and during generation of the vacuum. The vibration frequency ranges between 5-100 Hz and the vibration amplitude ranges between 0.1-1 mm. The selected vibration amplitude is preferably dependent on the configuration of the evacuation chamber. For example, if the injection needle is introduced through apertures having a diameter of 1 mm, the generated vibrations may have an amplitude of 0.2 mm. Since vibrations may contribute to the afferent by generating pressure signals in pressure receptors of the skin, the generated vacuum level may be as low as 200 mmHg.

Figure 16:
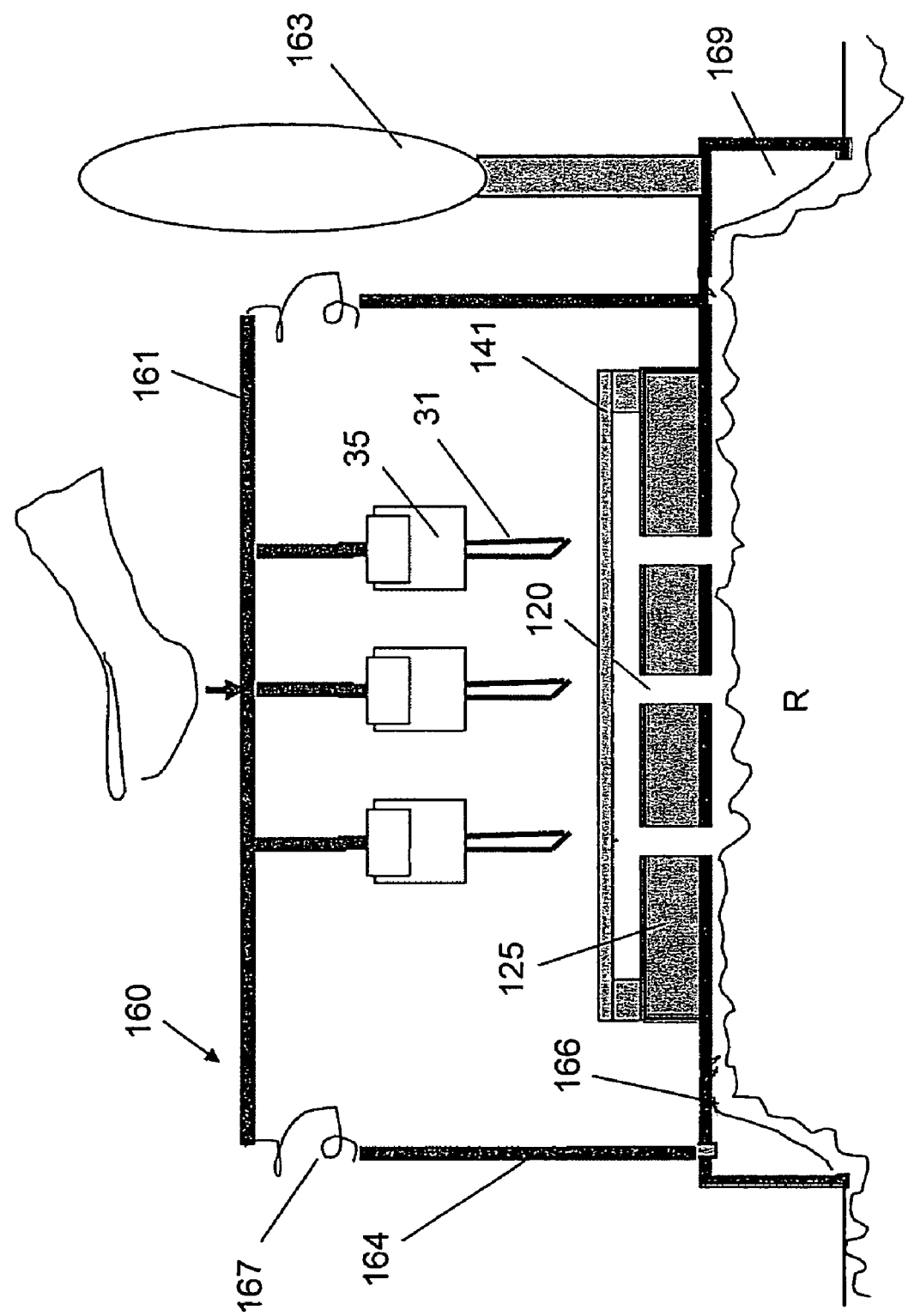
FIG. 16 schematically illustrates an apparatus for automatically administering a plurality of injection needles.

FIG. 16 illustrates an arrangement for automatically administering a plurality of injection needles. Apparatus 160 comprises horizontal bar 161 for holding a plurality of needle applicators 35 therebelow and a guide track 164 perpendicular to bar 161. Guide track 164 is connected to, or integrally formed with, cover element 166 of evacuation chamber 169. Engagement means (not shown) are provided for coupling bar 161 to guide track 164 to ensure proper alignment of each injection needle 31 with respect to an underlying aperture 120 of interface element 125, which is provided with a removable shield element 141. Actuation means (not shown) are provided to lower bar 161, in synchronization with the application of the vacuum to evacuation chamber 169, so that each needle 31 will be introduced through corresponding aperture 120 and be injected within skin region R. Apparatus 160 may be disposable and may employ a vacuum cylinder 163 having a considerably larger volume than that of evacuation chamber 169, e.g. a volume 10 times as great as the volume of evacuation chamber 169. Vacuum cylinder 163 may be activated by breaking breakable stop or by means of a skin contact detector, such as a microswitch or an optocoupler (not shown). Bar 161 may be spring biased by springs 167 to be raised above interface element 125 prior to injection.

Example 1

The pain level distribution resulting from a light-based, vacuum-assisted skin flattening skin treatment was compared to that resulting from a conventional light-based skin treatment. The light that was generated was suitable for hair removal, emitting pulses of light which were absorbed by hair follicles. The sharp burn sensation that was felt when a vacuum was not applied simulated the pain sensation which is normally associated with the injection of a needle through a skin region.

Light generated by an IPL Lovely unit manufactured by Msq Ltd., Israel and having an energy density of 18 J/cm$^2$, a wavelength greater than 640 nm, and a pulse duration of 30 msec was directed to 41 different skin targets. Light generated by an Alexandrite laser unit having an energy density of 25 J/cm$^2$ and a pulse duration of 3 msec was directed to 2 different skin targets. Light generated by a diode laser having an energy density of 42 J/cm$^2$ and a pulse duration of 2 msec was directed to 2 different skin targets. To 27 of those skin targets a vacuum of 500 mmHg was applied by means of a vacuum chamber having a planar, 20×50 mm sapphire rigid surface such that the skin target was flattened by the rigid surface. The skin treatment of the remaining 18 targets was performed without generation of a vacuum.

Figure 11:
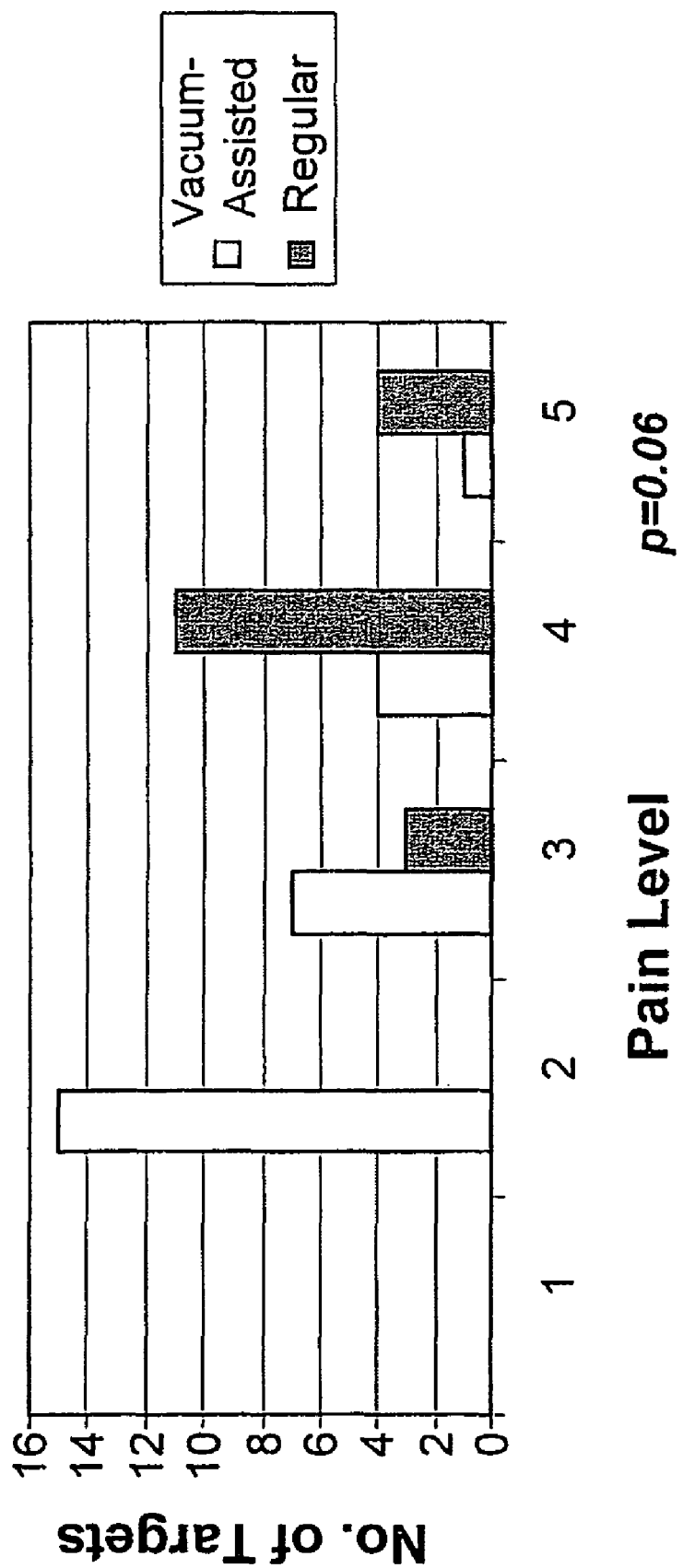
FIG. 11 illustrates a bar chart of the pain level distribution of patients that underwent light-based skin treatments, comparing the pain sensation of a vacuum-assisted treatment with a treatment that was not vacuum-assisted.

FIG. 11 illustrates a bar chart reflecting the pain sensation of patients that underwent each of the 45 skin treatments. The pain sensation was evaluated according to a modified McGill pain questionnaire and was categorized according to the Chi-square statistical technique with a deviation p of 0.06. Of the 18 skin targets that were not subjected to a vacuum, 4 (22.2%) were perceived as having a Pain Level of 5, 11 (61.1%) were perceived as having a Pain Level of 4, and 3 (16.7%) were perceived as having a Pain Level of 3. Of the 27 skin targets that were subjected to a vacuum that is capable of inducing skin flattening, 1 (3.7%) was perceived as having a Pain Level of 5, 4 (14.8%) were perceived as having a PainLevel of 4, 7 (25.9%) were perceived as having a Pain Level of 3, and 15 (55.6%) were perceived as having a Pain Level of 2. Thus the majority of targets which were not subjected to a vacuum perceived a Pain Level of 4, which is very painful, while the majority of targets that were subjected to a vacuum perceived a Pain Level of 2, which is nearly without any pain. A patient undergoing a vacuum-assisted skin flattening skin treatment may therefore therefore anticipate a dramatic pain reduction.

Example 2

The influence of the vacuum level during a skin flattening skin treatment on the perceived pain level was tested. Light generated by an IPL Lovely unit manufactured by Msq Ltd., Israel and having an energy density of 18 J/cm$^2$, a wavelength greater than 640 nm, and a pulse duration of 30 msec was directed to 10 different skin targets. The pain sensation was evaluated according to a modified McGill pain questionnaire. Table I below reflects the average pain level reduction that was perceived for the different vacuum levels that were applied to each of the 10 skin targets.

At a vacuum level of approximately 150 mmHg, the perceived average pain level was 4. The perceived pain level was further reduced to a pain level of 3 when a vacuum level of 300 mmHg was applied, and a significant pain reduction to a pain level of 2 was achieved when a vacuum level of 500 mmHg was applied.

TABLE I

| Applied Vacuum (mmHg) | Level of Pain Reduction |
| --- | --- |
| 0 | 0 |
| 100 | 0 |
| 200 | 0 |
| 300 | 1 |
| 400 | 1 |
| 500 | 2 |

Example 3

The influence of the surface area of the transmitting element during a skin flattening skin treatment on the perceived pain level was tested. Light generated by an IPL Lovely unit manufactured by Msq Ltd., Israel and having and energy density of 18 J/cm$^2$, a wavelength greater than 640 nm, and a pulse duration of 30 msec was directed to 10 different skin targets. Light generated by a diode laser having an energy density of 42 J/cm$^2$ and a pulse duration of 2 msec was directed to 2 different skin targets. The vacuum level that was applied to each of the skin targets was 500 mmHg. The pain sensation was evaluated according to a modified McGill pain questionnaire.

For a rigid surface of 9×9 mm, the average perceived pain level was 3. For a rigid surface of 12×20 mm, the average perceived pain level was a tolerable 2-3. For a rigid surface of 20×40 mm, the average perceived pain level was 1-2, which was nearly without any pain.

Example 4

Since afferent inhibition in the dorsal horn may be limited to a few seconds, a test was conducted to determine the pain inhibiting influence of the delay between the time at which the target skin region was compressed and the time at which the target skin region was injected. Following each application of a 400 mmHg vacuum level to the evacuation chamber, a sharp needle pierced the interface element of the evacuation chamber and was pressed on the target skin region. The needle was pressed on the target skin region following various time delays ranging from 1-7 seconds after the skin region was flattened. When the delay was less than 3 seconds or greater than 6 seconds, the pain sensation was not inhibited.

Example 5

The capability of a planar apertured interface element for maintaining a vacuum for a sufficiently long duration within an evacuation chamber to enable the administration of painless injections, despite the presence of the apertures within the interface element, was tested. A vacuum level of 0.5 atm was applied to the evacuation chamber. The interface element, which had a length and width of 12 mm, was formed with 4 apertures having a 1-mm diameter. The upward vacuum-generated force was therefore a product of the surface area of the evacuation chamber, which was approximately 144 mm$^2$, and the vacuum level of 0.5 atm, equaling a value of 72 atm-mm$^2$. The pressure differential generated downward force applied through the apertures onto the skin on which the evacuation chamber was placed was therefore a product of the total surface area of the apertures, which was approximately 3.1 mm$^2$, and the ambient pressure level of 1 atm, equaling a value of 3.1 atm-mm$^2$, which is considerably smaller than the upward vacuum-generated force. The distance between each aperture was 8 mm, and the drawn skin region was sufficiently compressed against the solid portions of the interface element to ensure afferent inhibition. The vacuum was able to be maintained within the evacuation chamber for a duration of greater than 1 minute.

Example 6

The pain inhibiting capability of an evacuation chamber having an interface element with a surface area of 25×40 mm was tested. The pain sensation of two patients, to whom an injection of 1 cc of 1% lydocaine was administered, was evaluated according to a modified McGill pain questionnaire. The normal pain sensation during injection when an evacuation chamber was not employed was compared with the pain sensation resulting from an injection administered via the interface element having a surface area of 25×40 mm, when a vacuum level of 600 mmHg was generated within the evacuation chamber. A total of 10 skin regions within the two patients were injected, wherein 6 injections were vacuum assisted and 4 injections were administered when a vacuum was not generated within the evacuation chamber. With respect to all 4 injections that were not vacuum assisted, the sensed Pain Level was 4. With respect to all 6 vacuum assisted injections, the sensed Pain Level was 2. The effect of lydocaine, which is a local anesthetic typically administered prior to biopsies, was noticeable for substantially the same duration within the drawn skin region as within a non-flattened skin region, indicating that the rate of intradermal material transport was not affected by the change in volume of the drawn skin region.

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims.

The invention claimed is:

1. An apparatus which is adapted to inhibit pain signals generated by pain receptors in the skin during a skin related medical treatment from being transmitted to the brain by inducing a controlled compression of a skin region, comprising:
   a) an evacuation chamber comprising an essentially rigid interface element through which a medical treatment can be administered to a selected skin region, one or more walls which are placeable on, or in the vicinity of, said skin region, an interior defined by at least said one or more walls and by said interface element, and an opening at the bottom of said interior which is sealable by said skin region;
   b) means for generating a vacuum within said evacuation chamber interior, the level of the generated vacuum being suitable for drawing said skin region through said opening towards, and in a compressing relation against, said interface element, whereby to inhibit the transmission of a pain signal generated by pain receptors located within said skin region; and
   c) means for administering a skin related medical treatment, said administering means adapted to pass through said interface element and to be directed to said compressed and pain inhibiting skin region,
   wherein the evacuation chamber is configured as a slit defined by the one or more walls, the one or more walls being elongated, planar sidewalls, the interface element being a rigid upper surface extending between, and having a considerably shorter length than, said sidewalls, at least one wall being a second interface element through which the medical treatment can be administered to the selected skin region.

2. The apparatus of claim 1, wherein the surface area of the interface element is greater than a threshold surface area suitable for inhibiting the transmission of a pain signal generated by pain receptors located within the skin region.

3. The apparatus of claim 2, wherein the threshold surface area is at least 100 mm$^2$.

4. The apparatus of claim 2, wherein the vacuum level within the evacuation chamber is greater than a threshold vacuum level suitable for inhibiting the transmission of a pain signal generated by pain receptors located within the skin region.

5. The apparatus of claim 4, wherein the threshold vacuum level is at least 150 mmHg.

6. The apparatus of claim 5, wherein the threshold vacuum level is at least 400 mmHg.

7. The apparatus of claim 1, wherein the vacuum generating means comprises a vacuum pump in fluid communication with the evacuation chamber.

8. The apparatus of claim 7, wherein the vacuum pump is a dual air-gel vacuum pump.

9. The apparatus of claim 1, wherein the vacuum generating means is a vacuum source in fluid communication with the evacuation chamber and means for isolating said vacuum source from the evacuation chamber interior.

10. The apparatus of claim 9, wherein the volume of the vacuum source is at least twice the volume of the evacuation chamber.

11. The apparatus of claim 1, further comprising control means for synchronizing the activation of the vacuum generating means.

12. The apparatus of claim 11, wherein the control means is a mechanical control means.

13. The apparatus of claim 11, wherein the control means comprises a controller and a skin contact detector in communication with said controller for sensing the placement of the evacuation chamber onto the skin region, said controller adapted to generate a first signal for activating the vacuum generating means following placement of the evacuation chamber onto the skin region and to generate a second signal for deactivating the vacuum generating means a predetermined duration following generation of said first signal.

14. The apparatus of claim 13, wherein the duration of the generated vacuum is no longer than approximately 6 seconds.

15. The apparatus of claim 13, wherein the control means further comprises a pressure sensor in fluid communication with the interior of the evacuation chamber and in electrical communication with the controller, the controller being further adapted to control the operation of the vacuum generating means so that a predetermined pain inhibiting vacuum level ranging between 400 mmHg and 1 atmosphere will be generated within the evacuation chamber.

16. The apparatus of claim 13, wherein the vacuum generating means comprises at least one control valve, the controller being suitable for delivering air through said at least one control valve in order to increase the pressure in the evacuation chamber to atmospheric pressure following the generation of the second signal, to allow for effortless repositioning of the evacuation chamber to a second skin region, the control means being selected from the group of electronic means, pneumatic means, electrical means, and optical means.

17. The apparatus of claim 9, wherein the skin contact detector is an opto-coupler or a microswitch.

18. The apparatus of claim 1, wherein the interface element is pre-compressed.

19. The apparatus of claim 1, wherein the interface element is planar.

20. The apparatus of claim 1, wherein the interface element is curvilinear.

21. The apparatus of claim 1, wherein the means for administering the medical treatment is an injection needle.

22. The apparatus of claim 21, wherein the interface element is puncturable.

23. The apparatus of claim 22, wherein the interface element is a subdivided interface element.

24. The apparatus of claim 21, wherein the interface element is an apertured interface element, an injection needle being introducible through each of said apertures.

25. The apparatus of claim 24, further comprising means for maintaining the vacuum within the evacuation chamber following termination of the vacuum generating means.

26. The apparatus of claim 25, wherein the vacuum maintaining means comprises a plurality of rims connected to the underside of the apertured interface element, each of said rims encircling a corresponding aperture formed in the interface element and adapted to produce a volume of negative pressure within the evacuation chamber for drawing the skin region in compressing relation against the interface element following termination of the vacuum generating means, said volume being enclosed by the interface element, rim, and drawn skin region or being enclosed by the interface element, evacuation chamber sidewall, and drawn skin region.

27. The apparatus of claim 24, wherein the total area of the apertures is less than 20% of the total area of the interface element.

28. The apparatus of claim 24, wherein the apertures are covered by a shield element.

29. The apparatus of claim 28, wherein the shield element is placed directly on top of the interface element.

30. The apparatus of claim 28, wherein a seal element is interposed between the shield element and the interface element.

31. The apparatus of claim 28, wherein marks corresponding to the location of the apertures are indicated on the upper face of the shield.

32. The apparatus of claim 24, further comprising means for guiding the injection needle through an aperture to the drawn skin region.

33. The apparatus of claim 32, further comprising means for administering a plurality of injection needles.

34. The apparatus of claim 33, wherein the means for administering a plurality of injection needles comprises a bar for holding a plurality of needle applicators therebelow and a guide track substantially perpendicular to said bar.

35. The apparatus of claim 1, further comprising a vibrator kinematically connected to the interface element.

36. The apparatus of claim 1, wherein the means for administering the medical treatment is a beam of ultrasonic waves and the interface element is made of a material which is transparent to ultrasonic waves.

37. The apparatus of claim 36, wherein the ultrasonic waves have a frequency ranging from 1 to 10 MHz and are generated by means of an ultrasonic transducer.

38. The apparatus of claim 1 wherein the means for administering the medical treatment is a pulsed source of electromagnetic energy for generating waves that are transmitted through the interface element.

39. The apparatus of claim 38, wherein the pulsed source of electromagnetic energy is a laser or intense pulsed light (IPL) light source.

40. The apparatus of claim 38, wherein the electromagnetic energy has a wavelength ranging from 400 to 1800 nm.

41. The apparatus of claim 38, wherein each wall of the evacuation chamber is puncturable, a darkened needle capable of piercing a wall of the evacuation chamber, attracting the electromagnetic energy, and thermally damaging the surrounding skin structure.

42. The apparatus of claim 38, wherein the electromagnetic energy has an energy density ranging from 10 to 100 $J/cm^2$ and a pulse duration ranging from 10 to 300 milliseconds.

43. The apparatus of claim 1, further comprising a gliding apparatus for moving the pulsed source of electromagnetic energy over the interface element at a speed ranging from 0.3 to 40 cm/sec.

44. The apparatus of claim 43, wherein the pulsed source of electromagnetic energy is moved by means of an optical detector that senses the presence of a marker on the interface element.

45. The apparatus of claim 43, wherein the pulsed source of electromagnetic energy is moved by means of a texture sensing mechanism.

46. The apparatus of claim 1, wherein the interface element is an apertured interface element, the electromagnetic energy propagating through each of the apertures without being transmitted through the material from which the interface element is composed.

47. The apparatus of claim 46, wherein the pulsed source of electromagnetic energy is a $CO_2$ laser or an Erbium laser.

48. An apparatus which is adapted to inhibit pain signals generated by pain receptors in the skin during a skin related medical treatment from being transmitted to the brain by inducing a controlled compression of a skin region, comprising:
   a) an evacuation chamber comprising an essentially rigid interface element through which a medical treatment can be administered to a selected skin region, one or more walls which are placeable on, or in the vicinity of, said skin region, an interior defined by at least said one or more walls and by said interface element, and an opening at the bottom of said interior which is sealable by said skin region;
   b) means for generating a vacuum within said evacuation chamber interior, the level of the generated vacuum being suitable for drawing said skin region through said opening towards, and in a compressing relation against, said interface element, whereby to inhibit the transmission of a pain signal generated by pain receptors located within said skin region; and
   c) means for administering a skin related medical treatment, said administering means adapted to pass through said interface element and to be directed to said compressed and pain inhibiting skin region,
   wherein the vacuum generating means is a vacuum source in fluid communication with the evacuation chamber and means for isolating said vacuum source from the evacuation chamber interior,
   wherein the vacuum source is a pre-evacuated container,
   wherein the isolation means is openable by control means, and
   wherein the control means comprises a pin placeable on the skin region, the pointed end of said pin adapted to pierce a membrane stretched across the interior of a conduit extending between the pre-evacuated container and the evacuation chamber once the evacuation chamber is placed on the skin region.

49. The apparatus of claim 48, wherein the isolation means is a valve.

50. The apparatus of claim 48, wherein the isolation means is a breakable stop.

51. The apparatus of claim 48, wherein the control means is a controller and a skin contact detector in communication with said controller for sensing the placement of the evacuation chamber onto the skin region, said controller adapted to generate a signal for opening the isolation means following placement of the evacuation chamber onto the skin region.

52. The apparatus of claim 48, wherein the control means further comprises a valve in communication with both the conduit and surrounding ambient air, said valve being openable whereby to release the vacuum by kinematic means a predetermined period of time following placement of the evacuation chamber on the skin region.

53. The apparatus of claim 48, wherein the pre-evacuated container is integrally connected to the evacuation chamber.

\* \* \* \* \*